US012773434B2

(12) United States Patent
Amin et al.

(10) Patent No.: US 12,773,434 B2
(45) Date of Patent: Oct. 27, 2026

(54) METHODS FOR LYOPHILIZED KEFIR-LOADED SELF-NANOEMULSIFYING DELIVERY SYSTEM OF CARAWAY OIL AND LICORICE EXTRACT ON COGNITIVE FUNCTION VIA THE MICROBIOTA-GUT-BRAIN AXIS

(71) Applicant: UNIVERSITY OF SHARJAH, Sharjah (AE)

(72) Inventors: Amr Amin, Sharjah (AE); Mai Mamdouh Anwar, Cairo (EG); Amira A. Boseila, Kantara Branch (EG)

(73) Assignee: UNIVERSITY OF SHARJAH, Sharjah (AE)

( * ) Notice: Subject to any disclaimer, the term of this patent is extended or adjusted under 35 U.S.C. 154(b) by 0 days.

(21) Appl. No.: 19/308,610

(22) Filed: Aug. 25, 2025

(65) Prior Publication Data

US 2026/0183352 A1 Jul. 2, 2026

Related U.S. Application Data

(60) Provisional application No. 63/740,040, filed on Dec. 30, 2024.

(51) Int. Cl.

| | |
|---|---|
| ***A61K 35/747*** | (2015.01) |
| ***A01P 1/00*** | (2006.01) |
| ***A61K 9/107*** | (2006.01) |
| ***A61K 9/19*** | (2006.01) |
| ***A61K 35/20*** | (2006.01) |
| ***A61K 36/236*** | (2006.01) |
| ***A61K 47/10*** | (2017.01) |
| ***A61K 47/26*** | (2006.01) |
| ***A61P 25/28*** | (2006.01) |
| ***A61P 29/00*** | (2006.01) |

(52) U.S. Cl.

CPC .............. *A61K 35/747* (2013.01); *A01P 1/00* (2021.08); *A61K 9/1075* (2013.01); *A61K 9/19* (2013.01); *A61K 35/20* (2013.01); *A61K 36/236* (2013.01); *A61K 47/10* (2013.01); *A61K 47/26* (2013.01); *A61P 25/28* (2018.01); *A61P 29/00* (2018.01)

(58) Field of Classification Search

CPC ........................................................ A61K 9/19

See application file for complete search history.

(56) References Cited

FOREIGN PATENT DOCUMENTS

WO WO-2009132342 A1 * 10/2009 .............. A61P 31/10

OTHER PUBLICATIONS

Cruz et al., J. Braz. Chem. Soc., 2025; 36(4):1-11 (Year: 2025).*
Paula et al., Trends in Food Science & Technology, 2021; 116:370-386 (Year: 2021).*
Brialy et al., Folia Microbiol, 1995; 40(2):198-200 (Year: 1995).*
Mitra et al., International Journal of Dairy Technology, 2020; 73(2):384-391 (Year: 2020).*
Anwar et al., Antioxidants, 2024; 13(1205):1-32 (Year: 2024).*

* cited by examiner

*Primary Examiner* — Brian Gangle
*Assistant Examiner* — Lakia J Jackson-Tongue
(74) *Attorney, Agent, or Firm* — MH2 Technology Law Group, LLP

(57) ABSTRACT

Chronic inflammatory bowel disorders (IBDs) are characterized by altered intestinal permeability, prompting inflammatory, oxidative stress and immunological factors. Gut microbiota disorders impact brain function via the bidirectional gut-brain axis, influencing behavior through inflammatory cascades, oxidative stress, and neurotransmitter levels. The present invention comprises lyophilized milk kefir alone and lyophilized milk kefir as solid carriers loaded with self-nanoemulsifying self-nanosuspension (SNESNS) of licorice extract. Daily administration of lyophilized milk kefir loaded with SNESNS restores normal body weight and intestinal mucosa while significantly reducing submucosal inflammatory cell infiltration, leading to significant alleviation of neurotransmitter levels and improved memory functions, thereby addressing gut-brain axis disorders. Additionally, it normalized fecal microbiome constituents, inflammatory cytokine levels, and oxidative stress in examined tissues and serum. Moreover, daily administration of kefir-loaded SNESNS normalizes the disease activity index, alleviates histopathological changes induced by IBD induction, and partially restored the normal gut microbiota. These alterations are associated with improved cognitive functions, attributed to the maintenance of normal neurotransmitter levels and alleviation of triggered inflammatory factors and oxidative stress levels.

14 Claims, 24 Drawing Sheets

B

C

A

A

B

E

A

METHODS FOR LYOPHILIZED KEFIR-LOADED SELF-NANOEMULSIFYING DELIVERY SYSTEM OF CARAWAY OIL AND LICORICE EXTRACT ON COGNITIVE FUNCTION VIA THE MICROBIOTA-GUT-BRAIN AXIS

TECHNICAL FIELD

The present invention relates to novel self-nanoemulsifying system (SNESNS) and methods of producing that uses lyophilized milk kefir grains as a solid carrier for bioactive compounds, specifically caraway oil and licorice extract for the enhancement of solubility, and effect of hydrophobic bioactive compounds that are helpful for reducing the risk of chronic diseases.

BACKGROUND OF THE INVENTION

The gut microbiome, often referred to as the "forgotten organ", has gained recognition for its profound influence on host physiology. Its composition varies based on the state of individual and the severity of disease. Recent estimates suggest that the gastrointestinal tract houses more than $10^{15}$ microorganisms, with the number of bacterial cells surpassing the number of host cells by a factor of ten. Moreover, the genetic materials of the microbiome outnumber the host genome by a factor of 100 or more [1]. The gut microbiota plays a vital role in regulating the gut-brain axis by secreting or triggering metabolites and proteins that facilitate the release of gut hormones and neuropeptides and the synthesis of neurotransmitters and their precursors. The human gut harbors thousands of bacteria, and their presence is crucial for bidirectional communication between the gut and the brain. These bacteria regulate immunological, endocrine, and neurological pathways, emphasizing their importance in gut-brain communication. Compared to individuals without similar diseases, patients with cognitive and neurodegenerative disorders display unique gut microbiomes and gut-brain axis anomalies. Additionally, the gut microbiome influences signals that shape immune functions, impacting normal metabolism and human physiology [2,3]. Inflammatory bowel disease (IBD) is an immune system-mediated inflammatory disorder primarily affecting the gastrointestinal tract. Conditions such as Crohn's disease (CD) and ulcerative colitis (UC) are encompassed within IBD. These disorders are linked to various contributing factors, including genetic, environmental, inflammatory, microbial, and oxidative stress conditions [4]. The intestinal mucosal barrier (IMB) serves as the primary mechanical, microbial, and immune barrier, preventing the entry of pathogenic molecules into the bloodstream. Individuals diagnosed UC consistently exhibit intestinal barrier dysfunction. This implies that UC is invariably associated with substantial damage to the integrity of the IMB, often due to an abnormal increase in certain types of pathogenic bacteria or a deficiency in beneficial bacteria [5]. Even minor damage to the intestinal barrier leads to a significant increase in intestinal permeability.

Recent research has underscored the significant impact of inflammatory bowel disease (IBD) on cognitive functions, revealing that patients with IBD are at an increased risk of experiencing cognitive decline and memory impairment. This association is primarily attributed to heightened oxidative stress, intestinal injury, and disruptions in the gut-brain axis [6]. The gut microbiota, which plays a crucial role in maintaining intestinal homeostasis, becomes dysbiotic in IBD, triggering local inflammatory responses and compromising the integrity of the intestinal barrier. This dysbiosis leads to systemic inflammation, which can cross the blood-brain barrier (BBB) and induce neuroinflammation [7]. Elevated levels of proinflammatory cytokines, such as TNF-α, IL-6, and IL-16, have been observed in the colon, brain, and serum of IBD patients, contributing to the pathogenesis of the disease and subsequent brain injury [8]. These cytokines are capable of entering the brain and disrupting its homeostasis, thereby contributing to cognitive deficits and memory issues. Moreover, chronic inflammation and oxidative stress in IBD can lead to neuronal damage and impaired synaptic plasticity, further exacerbating cognitive dysfunction [9-11]. Studies have also shown that the gut-brain axis plays a pivotal role in neurodevelopment and cognitive health, and disruptions in this axis due to IBD can have profound effects on brain function [12]. Therefore, understanding the mechanisms linking IBD to cognitive decline is critical for developing therapeutic strategies aimed at mitigating these neurological impacts.

Disruption of the intestinal mucosal immune bidirectional system, often as associated with UC, leads to an overproduction of proinflammatory cytokines, triggered proinflammatory microglia phenotype 1[88 ] and oxidative stress [13]. These inflammatory cytokines can reach the brain through systemic circulation, resulting in behavioral changes, cognitive decline, apoptosis, and neuroinflammation. Increased levels of neurotoxic substances such as nitric oxide and reactive oxygen species (ROS) contribute to this neuroinflammatory response [13-16]. Thus, the gut-brain axis describes a unique bidirectional communication system between the central nervous system (CNS) and the gastrointestinal tract. This complex axis involves various systems, including the autonomic nervous system, neuroimmune system, CNS, neuroendocrine system, and gut microbiota. Any modulation in the gut microbiota is suggested to be directly correlated with abnormal brain function and mental disorders [6,17,18]. The primary bidirectional link in the gut-brain axis involves the vagus nerve, often referred to as the "crossed neuroimmune interactions nerve"[19]. Consequently, dysbiosis in the gut microbiome is suggested to directly contribute to the progression of behavioral changes, cognitive decline, and neurodegenerative diseases [13,20].

IBD-like models are well-established instruments to evaluate how UC progresses and to mirror the emergence and development of associated illnesses. These IBD-like models'main mechanisms entail sequentially damaging the intestinal immunological barrier by oxidative stress and inflammatory triggers. A commonly known induced IBD-like model involves the addition of dextran sulfate sodium (DSS) to drinking water [21,22].

The understanding of the significance of bacteria and the gut microbiome for overall human health dates back more than 150 years, and fermented food types play a crucial role in this context. The fermentation process has been employed to preserve food, extend shelf life, and provide numerous health benefits. Beneficial microorganisms in fermented foods contribute to regulating digestive system disorders, modifying the composition of the intestinal microbiota, ensuring controlled intestinal permeability, and enhancing barrier functions [23-25]. Furthermore, fermented products contain a variety of bioactive compounds with antimicrobial, anti-inflammatory, and antioxidant activities. These properties contribute to the overall health-promoting effects associated with the consumption of fermented foods [26].

Probiotics, living microorganisms found in fermented products, offer several health benefits when consumed regularly [26]. Both *Lactobacillus* and *Bifidobacterium*, two significant lactic acid bacteria species, have been utilized as probiotics since Elie Metchnikoff's research in 1907 to treat a range of illnesses. These bacteria produce active metabolites such as vitamins, organic acids, and other bioactive compounds [27]. Probiotics support intestinal microbiota homeostasis by improving mucin synthesis, controlling cytokines, and acting as immunomodulators and potent anti-inflammatory agents [26, 27]. Given that the etiology of IBDs involves various immunological and inflammatory factors affecting the diversity and composition of the intestinal microbiota, alternative natural therapies are needed to effectively combat IBDs. Given that the etiology of IBDs involves various immunological and inflammatory factors affecting the diversity and composition of the intestinal microbiota, alternative natural therapies are needed to effectively combat IBDs [28, 29]. Current treatments often involve the use of corticosteroids, immunosuppressants, and biologics, which can have significant side effects such as increased susceptibility to infections, liver toxicity, and bone marrow suppression. Additionally, these medications may not be effective for all patients and can lose efficacy over time, necessitating 139-term, high-dose treatments that further increase the risk of adverse effects [30-32]. These challenges have led to the exploration of probiotics and adjuvant medicines in novel pharmaceutical forms designed to enhance their administration, and effect. Kefir is a sort of milk product that has undergone fermentation and is made up of various fungi, yeast, and bacteria that create grain structures. It originated at the Russian Caucasus mountains centuries ago and has various health benefits [33]. In addition to improving the gut microbiota composition, Kefir-fermented milk has antioxidant, anti-inflammatory, antimycotic, antitumor, and immunomodulatory effects [34-36]. The immune-modulatory action of kefir grains may be related to its direct action on the microbiota and/or its indirect effect through the bioactive compounds and metabolites produced during the fermentation of starter grains [33]. These metabolites are suggested to have direct healing effects on IBDs and gut-brain axis disorders due to their wide range of active biological properties [37]. The conventional therapeutics for treating IBD primarily consist of several anti-inflammatory and antioxidant agents. However, their immune system side effects, including both short-and long-term disabilities, limit prolonged use [21]. Therefore, there is an urgent need for more efficient, affordable, and alternative treatments.

BRIEF SUMMARY

The present invention relates to novel compositions and methods that comprise a self-nanoemulsifying drug delivery systems (SNEDDS) comprising anhydrous homogenous liquid mixtures consisting of oil, surfactant, drug, and co-emulsifier or solubilizer, which spontaneously form oil-in-water nanoemulsion of approximately 200 nm or less in size upon dilution with water under gentle stirring. In certain embodiments, diluting the final composition of the present invention comprising lyophilized milk kefir loaded with SNESNS of caraway oil and licorice, produces a colloidal solution where the caraway oil will be emulsified as a nanoemulsion. In certain embodiments, the present invention avoids phase separation between water-soluble constituents and caraway oil, which facilitates the administration of the final composition and improves customer compliance. In preferred embodiments, the final composition of the present invention acts directly in the stomach (i.e., on the gut microbiota). In more preferred embodiments, daily administration of kefir-loaded SNESNS in a subject result in a significant alleviation of neurotransmitter levels and improved memory functions, thereby addressing gut-brain axis disorders. Furthermore, it normalizes fecal microbiome constituents, inflammatory cytokine levels, and oxidative stress in tissues and serum, leading to improved cognitive functions.

BRIEF DESCRIPTION OF THE FIGURES

The accompanying drawings are not intended to be drawn to scale. In the drawings, each identical or nearly identical component that is illustrated in various figures is represented by a like numeral. For purposes of clarity, not every component may be labeled in every drawing. In the drawings.

DETAILED DESCRIPTION OF THE EMBODIMENTS

Definitions

Figure 1:
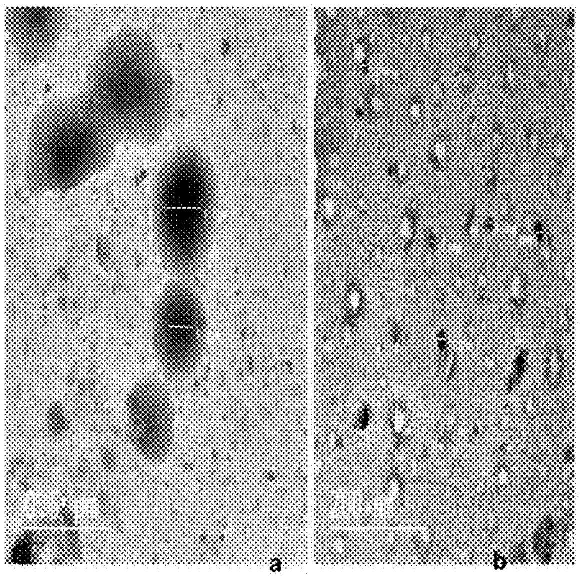
FIG. 1 illustrates Transmission Electron Microscopy (TEM) micrographs of the lyophilized Kefir-loaded licorice-SNESNS formulation. The images reveal the distinct morphology of the formulation, with black particles representing the nanosuspension (a), approximately 230-300 nm in size, formed after dilution with water. Additionally, smaller black droplets (b), measuring approximately 7-15 nm correspond to the nanoemulsion phase. These observations confirm the successful formation of a dual nanosystem, crucial for enhancing the bioavailability, administration, and stability of the bioactive compounds.

As used in this description and the accompanying claims, the following terms shall have the meanings indicated, unless the context otherwise requires:

As used herein, the singular forms "a, an" and "the" include plural references unless the content clearly dictates otherwise.

To the extent that the term "include," "have," or the like is used in the description or the claims, such term is intended to be inclusive in a manner similar to the term "comprise" as "comprise" is interpreted when employed as a transitional word in a claim.

The word "exemplary" is used herein to mean "serving as an example, instance, or illustration." Any embodiment described herein as "exemplary" is not necessarily to be construed as preferred or advantageous over other embodiments.

The term "subject" in accordance with the present invention, includes, e.g., mammals, such as dogs, cats, horses, rats, mice, monkeys, and humans.

The term "treatment" is used conventionally, e.g., the management or care of a subject for the purpose of combating, alleviating, reducing, relieving, improving, etc., one or more of the symptoms associated with a cancer, including all cancers mentioned herein.

The phrase "effective amount" indicates the amount of the compound which is effective to treat any symptom or aspect of the cancer. Effective amounts can be determined routinely. Further guidance on dosages and administration regimens is provided below.

The present invention pertains to a self-nanoemulsifying drug delivery system (SNEDDS) characterized by high stability and bioavailability of drug molecules or bioactive components. In embodiments, the present invention system generates nanodroplets for pharmaceutical applications with easy industrial scale-up due to simple formulation processes. In embodiments, the present invention comprises a self-nanoemulsifying self-nanosuspension (SNESNS) comprising a dual solubility enhancement method that combines the advantages of both nanoemulsions and nanosuspensions. SNESNS addresses the drawbacks of self-nanoemulsifying drug delivery systems, such as the inability to load high drug doses.

In one aspect, SNESNS comprises an isotropic mixture of oil, a surfactant, and a cosurfactant. In embodiments, the present invention comprises lyophilized milk kefir as a solid carrier for the conversion of liquid-SNESNS to solid-SNESNS.

In another embodiment, where oil-in-water nanoemulsion has a size of up to about 200 nm upon dilution with water under gentle stirring.

In another aspect, disclosed herein is a method for self-nanoemulsifying lyophilized milk kefir, comprising: (a) obtaining milk kefir grain starters; (b) adding the milk kefir grain starters to fully pasteurized milk'(c) fermenting the milk at about 25°°C. for about 24 hours; (d) filtering the milk through a sterile plastic sieve; (e) optionally storing the starter of the processed milk kefir grains under vacuum conditions at about 1 Pa and at a temperature of about −39° C. until needed for further use; (f) lyophilizing the milk kefir grain (L-MKG) using a freeze-dryer and optionally storing the lyophilized grains until needed for further use; (g) utilizing a ternary phase diagram for optimizing a ratio of formulation ingredients used for preparing a self-nano emulsifying system (SNES); (h) obtaining a self-nanoemulsifying formulation selected by utilizing the ternary phase diagram; (i) mixing Caraway oil, Tween 20, and propylene glycol in a formulation selected utilizing the ternary phase diagram; (j) adding licorice extract to obtain a final formulation; (k) mixing with a homogenizer for about 5 min to obtain a licorice-self-nanoemulsifying self-nanosuspension (SNESNS); (1)

adding the licorice-SNESNS dropwise to the milk kefir grains (L-MKGs) to obtain a homogenous dispersion; (m) lyophilizing the dispersion under reduced pressure to obtain lyophilized milk kefir as solid carriers loaded with self-nanoemulsifying self-nanosuspension (L-MKG/SNESNS) in powder form.

In certain embodiments, the present invention comprises Egyptian caraway, an oil composed mainly of limonene, β-selinene, β-elemene belemene and caryophyllene oxide. These bioactive compounds exhibit a number of advantageous biological characteristics, including antibacterial, antioxidant, anti-inflammatory, and anticonvulsant activities.

Introducing kefir probiotics and yeasts may initially cause gastrointestinal discomfort, such as bloating, gas, or stomach ache, as the gut microbiome adjusts to the new microbial population. Caraway (*Carum carvi*) oil is composed of various bioactive compounds, with the primary ones being: Carvone (50-70%), Limonene (20-30%), Pinene (5-10%), Myrcene (3-5%), and Linalool (1-3%). Caraway oil possesses carminative gas-relieving affects and antispasmodic properties, which can help alleviate symptoms of bloating, abdominal discomfort, and functional gastrointestinal disorders. The combination of caraway oil with milk kefir aims to counteract the potential gastrointestinal distress caused by probiotics.

In certain embodiments, the present invention comprises Licorice (Glycyrrhiza glabra), which has been widely utilized for many years in folk medicine. Licorice and its derived compounds show antiallergic, antibacterial, antiviral, anti-inflammatory, and antitumor effects. These pharmacological properties are exploited for the management of inflammatory disorders. The primary bioactive compounds found in licorice (Glycyrrhiza) extract are Glycyrrhizin (4-20%), flavonoids (such as liquiritin, isoliquiritin, liquiritigenin, and isoliquiritigenin), triterpenes (including glycyrrhetinic acid, 18β-glycyrrhetinic acid, and oleanolic acid), phenolic compounds (like ferulic acid, p-coumaric acid, and caffeic acid), and chalcones (e.g., echinatin and licochalcone A). In embodiments, to address the limitations of administering probiotics and SNESNS in liquid dosage forms, lyophilized milk kefir grain (L-MKG) was prepared and used as a solid carrier to be loaded with SNESNS of caraway oil and licorice extract (L-MKG/SNESNS). In preferred embodiments, the L-MKG/SNESNS comprises a solid self-nanoemulsifying composition with increases in solubility, absorption, effectiveness, and stability for the effective oral delivery of locally acting hydrophobic moieties.

In embodiments, the present invention reduces inflammatory processes, oxidative stress and cytokines production. Additionally, it improves behavioral abnormalities, cognitive decline, and decreased neurotransmitter levels in conjunction with different forms of histopathological damage of the brain while further contributing to mitigate inflammation in the intestinal tract. In preferred embodiments, the present invention improves gut-brain axis disorders and induces healing within the intestinal tract.

Homeostasis of the gut microbiota refers to maintaining a stable and balanced microbial composition within the host immune system. Persistent disruptions to this equilibrium can lead to dysbiosis, characterized by reduced diversity and depletion of beneficial microbes. Patients with IBD are prone to mental health issues such as anxiety, depression, and cognitive decline due to oxidative stress, intestinal injury, increased intestinal permeability, and gut-brain axis abnormalities. An imbalance in gut microbiota can trigger inflammatory responses in the intestines, damaging the intestinal barrier. This damage may allow pathogenic bacteria to enter the systemic circulation, leading to Blood-Brain Barrier (BBB) destruction, cognitive decline, and neuroinflammation.

The use of milk kefir grain starter requires specific procedures and inoculation to activate the grains correctly. We developed an efficient lyophilized nanoformulation of milk kefir grains. In certain embodiments, combining kefir with a self-nanoemulsifying system (SNESNS) containing caraway oil and licorice extract enhances the effect of these bioactive compounds. This increased localized effect leads to improved therapeutic outcomes compared to using kefir alone. In certain embodiments, the present invention simplifies the use of kefir by providing it in a lyophilized powder form, making it easier to store, handle, and administer, thus offering greater convenience for patients.

In certain embodiments, the method of the present invention eliminates the need for specific conditions and expertise required for the traditional preparation and activation of kefir grains. Lyophilization ensures the stability and consistency of the formulation, which is crucial for maintaining the therapeutic efficacy of the bioactive compounds. By converting kefir into a lyophilized form combined with nanoemulsified bioactive compounds, we overcome common barriers to traditional kefir use, such as the necessity for refrigeration and daily preparation. This makes the product more accessible and user-friendly, particularly for individuals who may not have the time or resources to manage traditional kefir fermentation.

Without being bound to any theory, the intestinal microbiota plays a crucial role in various diseases by directly interacting with the brain, immune system, and disease-related pathways involving the host's endocrine, nervous, and immune systems. In certain embodiments, the unique symbiotic mixture of microorganisms in kefir includes various strains that promote health by maintaining intestinal microbial balance and exerting anti-inflammatory and antioxidant effects. The present invention emphasizes the impact of IBD on the brain and the gut-brain microbiota and on cognitive disorders. In certain embodiments, daily administration of milk kefir grains restores and modulates the damage induced by IBD. In certain embodiments, early administration of L-MKG/SNESNS can restore impaired memory functions and behavioral changes due to brain injury, gut-brain axis dysfunction, and neuroinflammation.

Materials and Methods

Kefir Grain and Chemicals

A milk kefir grain starter was obtained from culture of health (150 Morrisville, NC, 27560-8591United States). Dextran sulfate sodium (DSS) and all other required chemicals of high analytical grade were purchased from Merck (Darmstadt, Germany) and Sigma-Aldrich (St. Louis, MO, USA). Caraway oil was purchased from Nefertari Oil (Cairo, Egypt); Tween 20 and propylene glycol (PG) were purchased from Sigma Aldrich (St. Louis, MO, USA); and licorice extract was a gift from the Egyptian Pharmaceutical Company (Alexandria, Egypt).

Lyophilized-Milk Kefir Grains (L-MKG)

Lyophilized milk kefir grains (L-MKG) were prepared through a multistep process. Initially, 20 grams of milk kefir grain starter is added to fully pasteurized milk and allowed to ferment at 25° C. for 24 hours. After fermentation, the milk is filtered through a sterile plastic sieve to separate it from the grains. To ensure the grains are clean for the next batch, they are thoroughly washed with pasteurized milk before each new inoculation [39-41]. The starter of the processed milk kefir grains was then stored under vacuum conditions at 1 Pa (Büchi Labortechnik AG, Flawil, Switzerland), maintaining a temperature of −39° C. This storage method preserves the grains' quality until they are needed. Finally, the grains are lyophilized using a freeze-dryer (Alpha 2-4, CHRIST, Osterode am Harz, Germany), resulting in lyophilized milk kefir grains (L-MKG). This freeze-drying process creates a stable, dry form of the grains that retains its properties for long-term use in experiments or other applications.

Detailed Lyophilization Conditions for Milk Kefir Loaded SNESNS (1) Initial Freezing Temperature: −40° C. for 6 hours; (2) load the frozen kefir into the lyophilizer; (3) Primary Drying Phase: set the temperature to about −30° C. and adjust the pressure at 0.5 mbar. Duration: 48 hours. (4) secondary Drying Phase: gradually increase the temperature to about 20° C. and keep the pressure at 0.5 mbar. This phase may last 10 to 15 hours [38, 39].

Construction of Ternary Phase Diagrams

The aim of ternary phase diagrams construction was to optimize the ratios of oil, surfactant, and co-surfactant in the formulation of the self-nano emulsifying system (SNES). The diagrams help identify the regions where stable and effective emulsions can be formed, ensuring the solubilization and bioavailability of the active compounds. This step is crucial for the development of a robust and reproducible formulation with enhanced therapeutic efficacy. The ternary phase diagram was created using Caraway oil (obtained from Agricultural Research Center, Giza, Egypt), Tween 20 (as a surfactant), and propylene glycol (as a cosolvent) purchased from Sigma-Aldrich (St. Louis, MO, USA) to detect the areas where each observed point could directly form a nanoemulsion upon dilution. Required mixtures were prepared with varying concentrations of these components, followed by the construction of the ternary phase diagram. Each point on the diagram underwent testing for its ability to self-emulsify by diluting a gram of the mentioned corresponding ternary mixture with distilled water up to 200 mL in a glass beaker. The mixture was then stirred magnetically at 37° C. for 5 minutes. Visual observation and inspection was employed to detect any phase separation in the diluted mixtures. Dispersion with a transparent appearance was categorized as falling within the nanoemulsion region [40].

Preparation of SNESNS From Licorice Extract

A self-nanoemulsifying formulation was selected from the ternary phase diagram to be used to prepare licorice-SNESNS. The formula composed of 30% Caraway oil, 60% Tween 20, and 10% propylene glycol (w/w) was prepared as follows: for each 150 gm of the formulation, 45 g of Caraway oil, 90 g of Tween 20 and 15 g of propylene glycol were mixed, and then 100 mL of the prepared mixture was mixed with 0.3 g of licorice extract (to yield a concentration of 3 mg/mL) obtained from (Sekem company, Cairo, Egypt) with the aid of homogenization for 5 min. The formula was prepared and subjected to further characterization [41].

Preparation of Solid SNESNS From Licorice Extract (L-MKG/SNESNS)

Ten milliliters of the prepared licorice-SNESNS formula was added dropwise to 25 mL of the milk kefir dispersion on a magnetic stirrer until a homogenous dispersion was obtained. The whole mixture was then lyophilized under reduced pressure to obtain lyophilized milk Kefir-loaded licorice-SNESNS in powder form In-Vitro Characterization of Licorice-SNESNS and L-MKG/SNESNS Particle size, Polydispersity Index (PDI), and Zeta Potential of L-MKG/SNESNS and Licorice-SNESNS:

The mean particle size and PDI of the prepared licorice-SNESNS and solid L-MKG/SNESNS 266 were measured using a Malvern Zetasizer 3000 (Grovewood Road, Malvern, Worcestershire, WR14 1XZ, UK) with a dynamic light-scattering mechanism. The measurements were performed in a quartz cuvette after each sample was diluted 100-fold with deionized water.

TEM

The morphologies of the prepared solid L-MKG/SNESNS and licorice-SNESNS were observed by TEM (JEOL, JEM-1230, Tokyo, Japan) after dilution with deionized water. A drop of the diluted samples was placed on a copper grid and stained with a 2% phosphotungstic acid solution Merck (Merck KGaA, Darmstadt, Germany) (FIG. 1). The excess staining agent was removed with the aid of filter paper, and then the grid was left to completely dry at ambient temperature.

Animals

Thirty healthy, pathogen-free male albino rats, each with a body weight ranging from 180 to 200 grams, were obtained from the animal house of the National Organization of Drug Control and Research (NODCAR). The rats had unrestricted access to standard laboratory chow and water during the whole experimental design and were subjected to specific environmental conditions, including a temperature of 25±1° C., humidity maintained between 50-70%, and a 12-hour light-dark cycle. The study was approved and adhered to guidelines for the animal ethical committee of the National Organization of Drug Control and Research (NODCAR) under the reference number (NODCAR/II/6/2023) and followed the principles of the 3Rs (Refine-Reduce-Replace). Before the experiment commenced, the rats were allowed to acclimate for one week to adapt to their surroundings. Throughout the study, all animals were provided unrestricted access to food and water. The ethical considerations and principles employed aimed at ensuring the well-being and humane treatment of the experimental animals.

Experimental Design

The thirty male albino rats were equally and randomly divided into the following groups each with 290 6 rats (n=6): (1) Group 1 (HCG): This group served as the control for the healthy control group (HCG) and consisted of rats administered water instead of the designed formulated milk kefir grains. (2) Group 2 (A-IBD-like model): This group included rats administered dextran sulfate sodium (DSS) at a concentration of 5% daily by oral gavage for 10 days to establish an acute IBD-like model [23-27,42,43]. The aim of conducting this group is to serve as an intermediate phase in our study. Its primary purpose is to demonstrate that, after ten days, the disease progresses to a chronic state in a cascading process. It was crucial to conduct the A-IBD-like model group for confirming the establishment and progression of the chronic IBD model before we evaluate the therapeutic effects of L-MKG and L-MKG/SNESNS treatments. By including this group, we can ensure that the chronic IBD model is accurately established, providing a solid foundation for assessing the efficacy of our treatments in the chronic phase of the disease. This intermediate phase is essential for understanding the cascade of disease progression and validating the chronic state as the target for our therapeutic interventions. (3) Group 3 (C-IBD-like model): This group included rats administered DSS (5%) daily by oral gavage for 16 days to establish a chronic IBD-like model [23-27,42-45]. (4) Group 4 (C-IBD like model+ L-MKG): This group included induced chronic IBD-like model rats administered DSS (5%) daily by oral gavage for 16 days [23-27,42-45], followed by treatment with lyophilized milk kefir Grains (L-MKG) for 10 days at a dose of 150 mg/kg via oral gavage [65]. The exact bioactive constituents in milk kefir grains have been previously demonstrated in other studies 311(5 ) Group 5 (C-IBD like model+ L-MKG/SNESNS): This group included induced chronic IBD-like model rats administered DSS (5%) daily by oral gavage for 16 days [23-27,42-64], followed by treatment with lyophilized milk kefir grains (L-MKG) loaded with SNESNS of licorice extract daily for 10 days at a dose of 100 mg/kg via oral gavage [46]. Each 100 mg of L-MKG/ SNESNS contains 10 mg caraway oil and 0.1 mg of licorice extract according to our prepared formulation.

Body Weight

The body weight of each rat in all five groups was documented at the conclusion of the experiment and compared with their initial weights recorded before the commencement of the experimental design. This approach was chosen to effectively assess the overall impact of the treatments on the rats'well-being. Monitoring body weight at the start and end of the experiment provides a clear and direct measurement of weight change, which is a critical indicator of the rats'health and response to the treatments. By comparing the initial and final weights, we can accurately evaluate the efficacy and any potential side effects of the treatments. This method is efficient and minimizes the handling of animals, reducing stress that could confound the experimental results. Additionally, this approach aligns with ethical considerations for animal welfare by limiting the frequency of interventions. Thus, the changes in body weight were documented after the experiment for each rat in all five groups, and the values were compared with their initial weights before the commencement of the experimental design [50,51].

Disease Activity Index

The Disease Activity Index (DAI) was utilized to evaluate the severity of colitis in the rat model. The DAI is a composite score based on three clinical parameters: weight loss, bleeding severity, and stool consistency. Weight loss was assessed and scored as follows: 0 points for no weight loss, 1 point for 5-10% weight loss, 2 points for 11-15% weight loss, 3 points for 16-20% weight loss, and 4 points for more than 20% weight loss. Bleeding severity was recorded as 0 points for no bleeding and 4 points for the presence of bleeding. Stool consistency was classified and scored as 0 points for normal stool, 2 points for loose stool, and 4 points for diarrhea. The DAI is calculated by summing the scores from these three categories, with the total score reflecting the overall disease severity. Higher DAI scores indicate more severe colitis. The specific methodology and scoring system used for this assessment are consistent with established practices described in the literature [52-57]. 341 Sample Collection, Processing, and Staining One day following the conclusion of the experimental design and one day prior to sacrifice through cervical dislocation, blood samples were collected from the retroorbital venous plexus and subsequently centrifuged at 1000×g for 10-15 minutes at 4° C. The resulting serum was then stored at −80° C. for future use. Stool samples were obtained from each rat in the respective groups on the same day before sacrifice. The stools were weighed and inoculated in 1% saline for subsequent biochemical detection. The brain, intestine, stomach, and colon were isolated and harvested from rats under the effect of isoflurane anesthesia (2-3% in 100% oxygen) (Acdima international, Cairo, Egypt) [58]. The brain, including the cortex and hippocampus, as well as the intestine, stomach, and colon, were then harvested. The colon's length was recorded. The isolated tissues were processed as follows: The brain (including the cortex and hippocampus) was fixed in 4% paraformaldehyde (PFA) (Sigma-Aldrich, St. Louis, MO, USA) and embedded in paraffin wax for hematoxylin-eosin (H&E) staining (Abcam Inc. 152 Grove Street Waltham, MA 02453 USA) and histopathological analysis. The small intestine, and stomach were also fixed in 4% PFA (Sigma-Aldrich, St. Louis, MO, USA), embedded in paraffin, and subjected to H&E staining. Additionally, sections of the small and large intestines were processed using trichrome staining (Abcam Inc., Waltham, MA, USA) to evaluate the amount or density of collagen fibers. This assessment helps indicate pathological changes or conditions affecting the tissue compared to the control group, following the methodologies described by Araruna et al. and Matei-Latju et al. [59,60]. Tissue samples were divided into two portions: one for preparation of tissue homogenates for biochemical 361 analysis and the other for histopathological examination.

Determination of Luminal Bacterial Concentrations

Cecal contents were collected from euthanized rats, and 1 ml of these contents was immediately weighed and prepared for analysis. The cecal samples were serially diluted in pre-reduced thioglycolate broth (Sigma-Aldrich, St. Louis, MO, USA) to maintain anaerobic conditions. From each dilution, 100 μl was plated on pre-reduced, anaerobically sterilized agar plates, which were incubated in an anaerobic chamber with an atmosphere of 5% CO2, 10% H2, and 85% N2. Additionally, blood agar plates were used to culture aerobic bacteria. The agar plates were incubated at 37° C., with aerobic cultures assessed after 2 days and anaerobic cultures after 6 days. Colonies were counted to determine bacterial concentrations in the cecal contents [80,81]. Detailed information regarding the primary isolation media and colonial appearance is available in the supplementary file. Identification of colitis bacteria To identify colitis-associated bacteria, the cecal contents were analyzed using the same plated samples and incubation conditions described in Section 2.12. After incubation, colonies were examined and characterized based on their morphology and growth patterns. Specific bacterial identification was performed using standard biochemical tests and, where applicable, using phase-contrast microscopy and a Neubauer counting chamber to accurately determine the presence of bacteria associated with colitis. This comprehensive approach allowed for detailed analysis of both aerobic and anaerobic bacterial populations in the cecal contents [61,62]

The identification of colitis-associated bacteria was carried out using a systematic approach. Initially, a quick oxidase test was performed on the cultured bacteria to determine the presence of cytochrome c oxidase. A single isolated colony from a pure culture was then selected and suspended in sterile distilled water. The API20E Biochemical Test Strip (BioMérieux, Marcy-l'Etoile, France) was used for further identification, which includes dehydrated bacterial media and biochemical reagents in 20 separate compartments. Each compartment was filled with the bacterial suspension using a Pasteur pipette, and sterile oil was added to specific compartments as required. The test strip was incubated at 37° C. for 18 to 24 hours. For result interpretation, color changes in the compartments were observed after incubation. Some compartments required additional reagents for color development: ferric chloride for TDA, Kovacs reagent for IND, and a combination of 40% KOH (VP reagent 1) and a-naphthol (VP reagent 2) for VP. Results were recorded using the API Reading Scale, where positive or negative marks were made for each test. The scores from triplets of wells were summed to generate a 7-digit code, which was used to identify the bacterial species by referencing the API catalog [63,64].

Behavioral Studies

In the behavioral studies, two distinct tests were employed to assess various aspects of rats behavior: The Tail Suspension Test (TST) is a well-established method primarily used to measure the duration of immobility in rodents when they are suspended by their tails. This immobility is considered indicative of behavioral despair, a model often used to evaluate antidepressant-like effects and depressive behaviors. While the TST is traditionally associated with assessing depressive behaviors, there is emerging evidence that it can also provide insights into broader cognitive aspects. Specifically, the TST can reveal how neuroimmune responses and emotional and motivational states influence cognitive processing. For instance, stress-related alterations in the neuroimmune system can affect both mood and cognitive functions, including memory and decision-making. This interplay suggests that the TST may reflect not only behavioral despair but also underlying changes in cognitive processes influenced by emotional and neuroimmune factors [65-69]. TST is traditionally more common in smaller rodents such as mice, recent literature supports its application in larger rodents including rats [89-93]. After completing the experimental phase, the TST was conducted on all rats the day before blood collection and tissue isolation. This involved placing each rat in a quiet, isolated square box equipped with a hook, suspending approximately 1 cm of its tail about 50 cm above the ground. The total suspension period was approximately 6 minutes, with the first 60 seconds designated as the adaptive latency time. The immobility period, recorded as the time when the rat ceased struggling, served as an indicator of anxiety and depression-like behavior. A shorter immobility period suggested greater susceptibility to these behavioral traits [70-74].

In the Y-maze test, an enclosed maze test was utilized to evaluate spatial memory and study cognitive functions, including those associated with the hippocampal region and cognitive decline. This test capitalizes on the inherent exploratory tendencies of animals, which naturally seek out new environments, making it ideal for assessing cognitive capabilities. It is particularly effective at identifying impairments in spatial recognition memory, which can be caused by factors like stress, neurological disorders, or pharmacological interventions [75-77]. The maze consisted of three arms forming a Y-shape, with two arms designated goal arms containing rewards. Doors at the entrance of each arm either confined the rat to specific arms or prevented entry into certain arms. The Y-maze leverages the rat's motivation to explore the surroundings and seek rewards. Healthy rats demonstrated the ability to remember previously entered arms, alternating to the opposite arm in subsequent trials. In contrast, aged and stressed rats exhibited challenges in remembering the correct choice of arms. Prior to the main test, a pretraining phase was conducted three times to familiarize the rats with the maze. The spontaneous alternation percentage (SAP) was then calculated from the total number of rat alternations divided by the number of arm entries minus 2, multiplied by 100:% SAP=[(number of rat alternations)/(number of arm entries−2)]×100. After each trial in both tests, the testing apparatus was consistently cleaned with 10% ethanol to maintain a standardized testing environment [70].

Myeloperoxidase (MPO) Activity Measurement

Myeloperoxidase activity in colon tissue homogenates was assessed following the method outlined by Bradley et al. [78] with certain modifications. The measurement of MPO activity (Abcam, Cambridge, UK) was expressed in units per gram of tissue (u/gm tissue).

Measurement of Proinflammatory Cytokines and Neurotransmitters

Proinflammatory cytokines, including TNF, IL-6, IL-B, and IL-10, were detected in both serum and tissue homogenate samples from the colon, intestine, and hippocampus according to the manufacturer's instructions (MyBioSource, San Diego, CA 92195-3308, USA). LPS levels were measured exclusively in the serum using an ELISA DAS LPS kit (Ingenasa, Hermanos García Noblejas, Madrid Spain). Acetylcholine, GABA, dopamine, 5-HT, and BDNF levels were specifically assessed in the hippocampus according to the manufacturer's instructions (MyBioSource, San Diego, CA 92195-3308, USA).

Detection of Oxidative Stress Biomarkers in Serum and Tissues

The oxidative stress biomarker malondialdehyde (MDA) was measured in the hippocampus, intestine, and colon following the methodologies described by Buege and Aust, Belguendouz et al., Levine et al., and Anwar et al. [79-83] and according to manfacturer instructions (Cayman Chemical Company, Ann Arbor, MI, USA). Enzymes such as SOD (Cayman Chemical Company, Ann Arbor, MI, USA), NO (Abcam, Cambridge, UK), and GST (Sigma-Aldrich, St. Louis, MO, USA) were also detected in the hippocampus, intestine, and colon according to Kakkar et al. [84], Miranda et al. [85], and Habig et al. [86], respectively to assess the degree of damage and alleviation among tissues.

Statistical Analysis

The data are presented as the mean±standard error of the mean (MSE) for the five groups. Statistical differences among the five groups were assessed using one-way analysis of variance (ANOVA) followed by Dunnett's test. Comparisons between groups were done using ANOVA with multiple comparisons post hoc test for normally distributed quantitative variables. For non-normally distributed quantitative variables, we utilized the Kruskal-Wallis test and the Mann-Whitney test. A significance level of $P<0.05$ was considered statistically significant. The statistical packages used for the analysis included SPSS, GraphPad, and Excel.

EXAMPLES

Construction of Ternary Phase Diagrams

Figure 2:
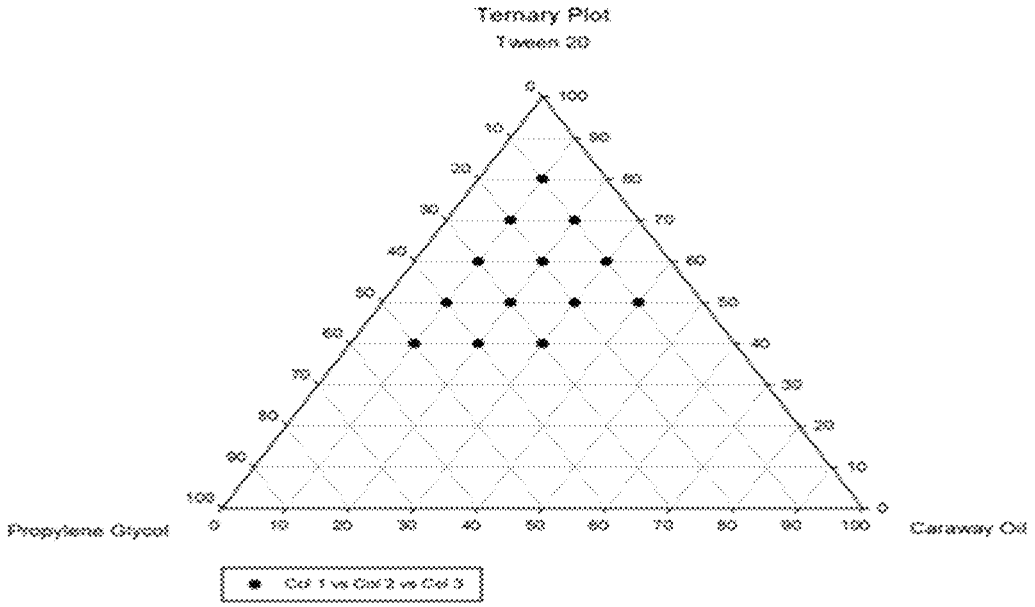
FIG. 2 illustrates a ternary phase diagram of caraway oil, tween 20 and PG where the dots indicate systems that form translucent or transparent nanoemulsion upon dispersion in water.

The ability of the formulations to self-emulsify upon dilution along with gentle agitation was tested. As illustrated by the results of the ternary phase diagram in FIG. 2, increasing the oil concentration by more than 30% led to a decrease in the self-nanoemulsifying ability of the system. Additionally, the Tween 20 concentration should be ≥40% to maintain the self-nanoemulsifying properties of the system. The rounded points represent all the self-nanoemulsifying properties of the system. The rounded points represent all the self-emulsifying formulations that could emulsify spontaneously in seconds and be infinitely diluted by water.

Particle Size Analysis and Zeta Potential of L-MKG/SNESNS and Licorice-SNESNS Hence, a formula composed of 30% Caraway oil, 60% Tween 20, and 10% PG was selected for drug loading because it contained a compromised surfactant/cosurfactant ratio and exhibited reasonable emulsification power upon dilution since it was crucial to adjust the Tween 20 concentration to be high enough to ensure self-emulsification of Caraway oil.

Figure 3:
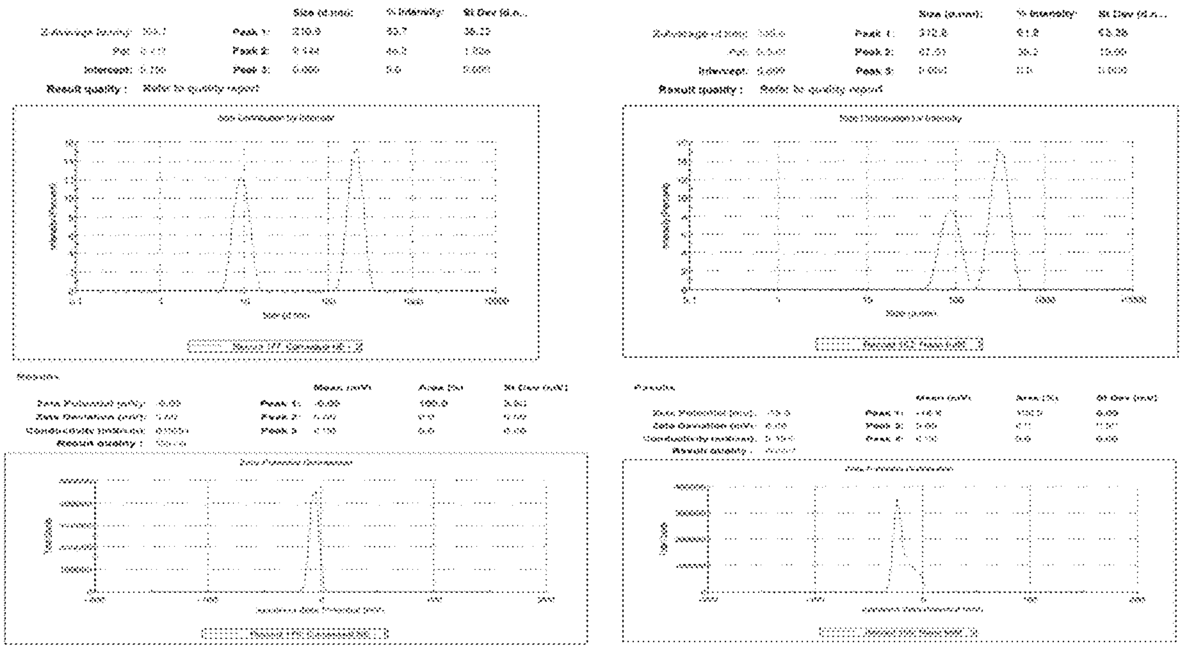
FIG. 3 illustrates particle size analysis and zeta-potential of licorice-SNESNS and lyophilized-Kefir loaded licorice-SNESNS.

The Z-average of the prepared licorice-SNESNS was 435.5±136 nm, while that of the L-MKG/SNESNS was 435.43±87.96. The PDI ranged between 0.45 and 0.48, indicating the heterogeneity of the particle size distribution. As depicted in Table (1) and FIG. 3, the particle size distributions of Licorice-SNESNS and L-MKG/SNESNS showed two size peaks with different intensities. For the licorice-SNESNS formulation, the peak with an average particle size of 9.31±0.27 (intensity of 46%) corresponds to the formed nanoemulsion globules. This peak shifted to a size of 114.6±24.7 when licorice-SNESNS was loaded on lyophilized milk fermented by the kefir grain. At the same time, the nanosuspension particles ranged in size between 202.93±31.32 and 422.1±96.93 nm for the licorice-SNESNS and L-MKG/SNESNS, respectively. Upon lyophilization, the size of the droplets increased due to increased adherence/adsorption of liquid droplets with probiotics of milk kefir grain [87].

The zeta potentials of the licorice-SNESNS and L-MKG/SNESNS were −6.13±1.02 and −18.1±0.61 mV, respectively. The increase in the negative charge of L-MKG/SNESNS is due to the presence of probiotic microorganisms such as acetic acid bacteria [88,89].

Morphological Analysis

Figure 4:
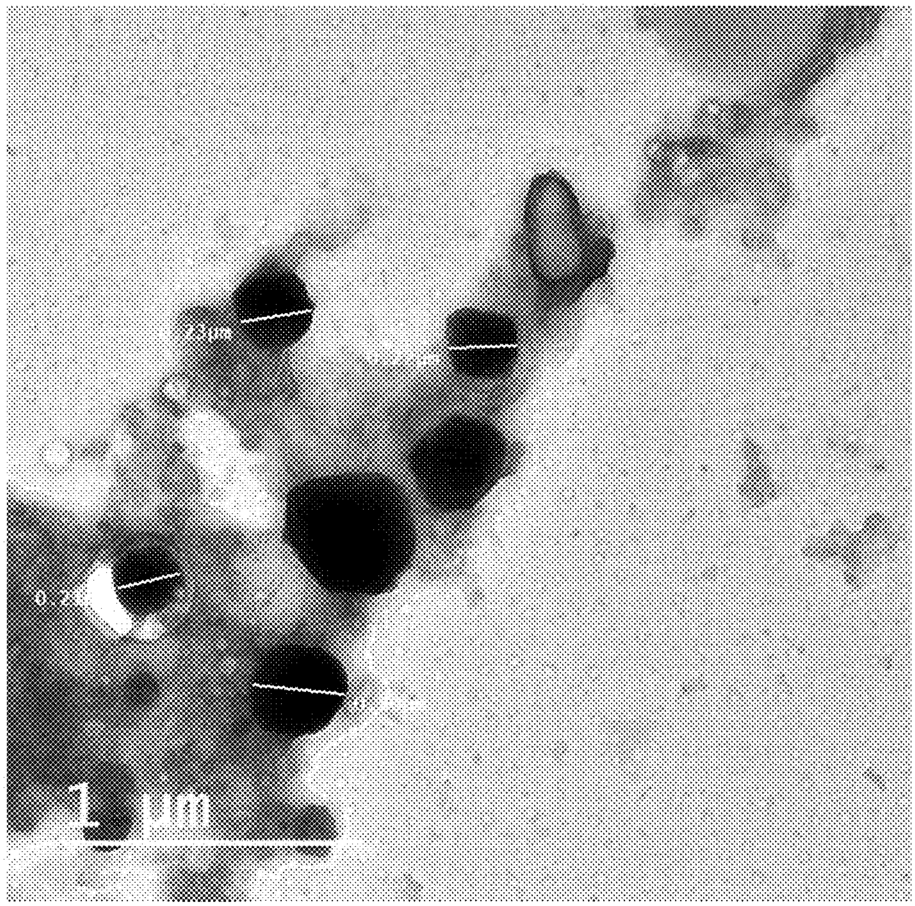
FIG. 4 illustrates TEM micrographs of lyophilized kefir loaded licorice-SNESNS formulation revealing black particles of the formed nanosuspension (~230-300 nm) after dilution with water along with black nanoemulsion (~7-15 nm) droplets of smaller droplet size.

TEM micrographs are shown in FIG. 4, The L-MKG/SNESNS formulation was able to form a double nanosystem (nanoemulsion and nanosuspension).

Assessment of Body Weight and Disease Severity

Figure 5A:
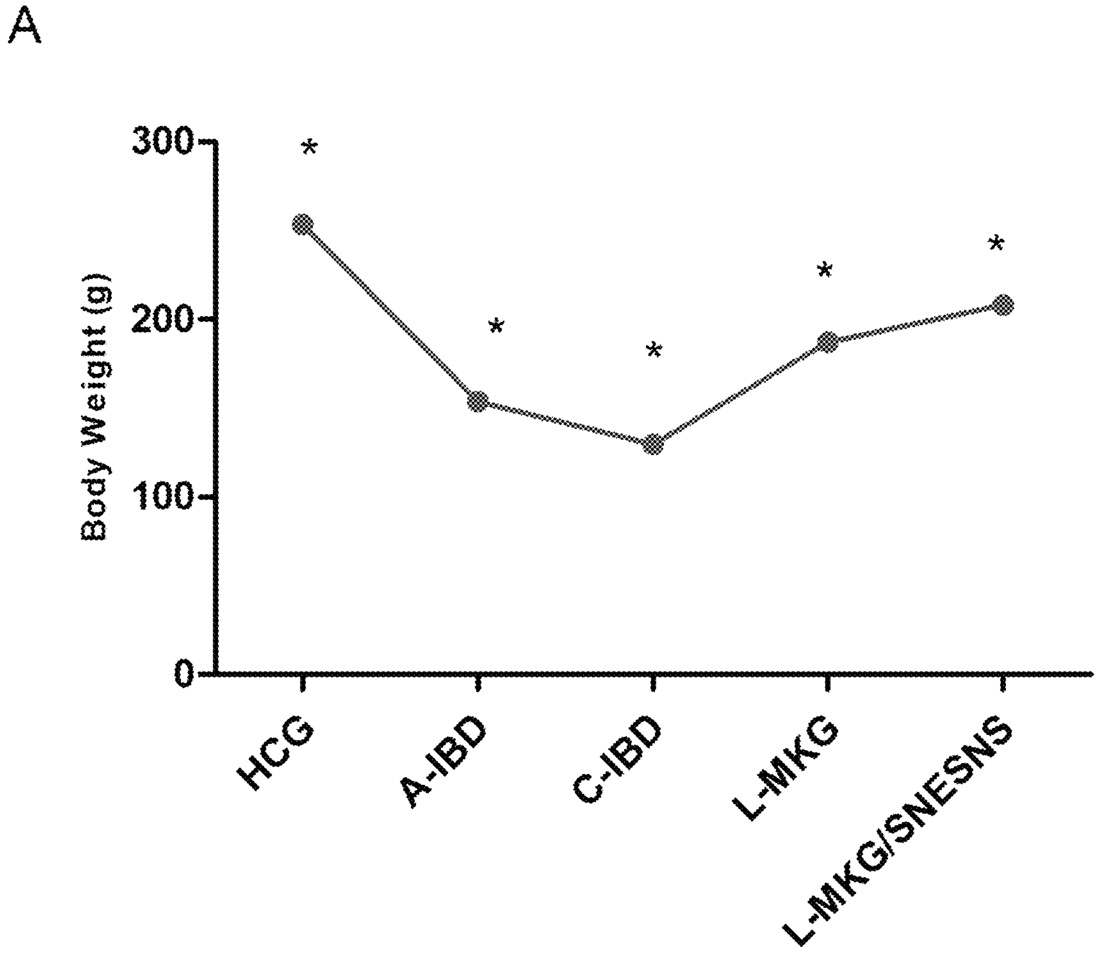
FIGS. 5A-5C illustrate the effect of Formulated L-MKG Administration in an IBD-DSS Induced Rat Model on body weight (FIG. 5A), Disease Activity Index (FIG. 5B), and colon length (FIG. 5C). Values are expressed as Mean±S.E. (n=6 Rats per group). Groups marked with the same asterisk indicate significance (*p<0.05). Groups abbreviations: HCG (Healthy Control Group), A-IBD (Acute Inflammatory Bowel Disease), C-IBD (Chronic Inflammatory Bowel Disease), L-MKG (lyophilized milk kefir), and L-MKG/SNESNS (lyophilized milk kefir as solid carriers loaded with self-nanoemulsifying self-nanosuspension).
Figure 5B:
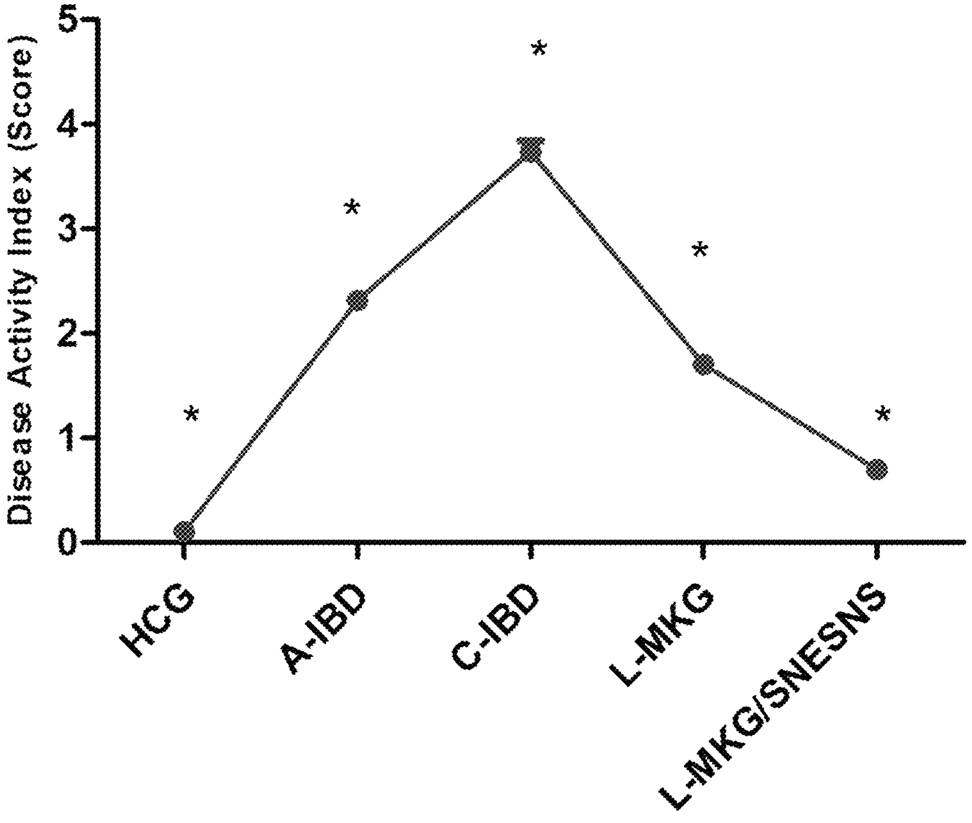
Figure 5C:
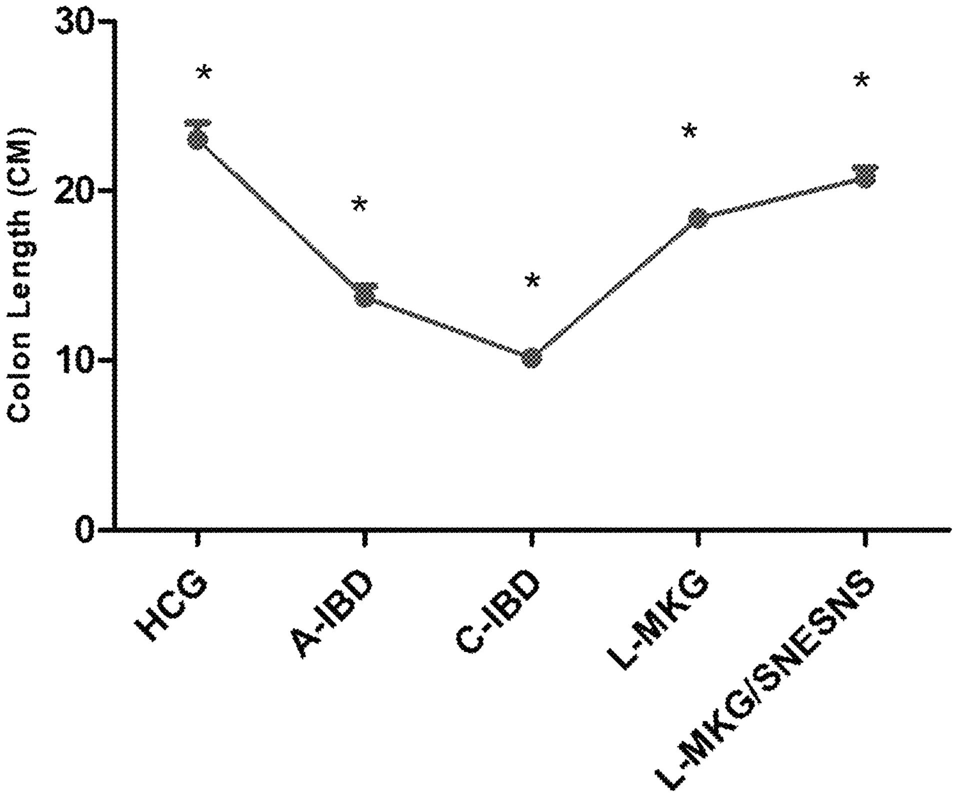

To investigate the impact of administering milk kefir grain beverages, whether in lyophilized or L-MKG/SNESNS formulations, on both acute and chronic inflammatory bowel disease (IBD) models, daily administration for 10 and 16 days led to notable effects. Both models were associated with reduced colon length, increased rectal bleeding, an elevated disease activity index (DAI), and altered stool consistency. These changes were more pronounced in the chronic IBD (C-IBD) group than in the acute (A-IBD) group compared to those in the healthy control group, as depicted in FIGS. 5A-5C.

In contrast, the daily administration of LMKG/SNESNS significantly mitigated all the above-mentioned drawbacks associated with the induction of chronic IBD and almost restored the levels to those observed in the control group ($P<0.05$). Furthermore, the administration of L-MKG alone significantly improved the colon length, DAI, and degree of weight loss. However, the administration of L-MKG/SNESNS resulted in even greater improvements, as illustrated in FIGS. 5A-5C.

Effect on Luminal Bacterial Concentration

Table 2 provides a quantitative analysis of luminal bacterial concentrations under different experimental conditions. The counts are expressed in colony-forming units per milliliter (cfu/ml). Symbols such as +, ++, and +++ denote varying levels of bacterial presence: +indicates low, ++moderate, and +++high bacterial counts. Conversely, "–" indicates no detectable bacterial count. Specifically, beneficial bacteria including *E. coli*, *Streptococcus mitis*, *Lactobacillus casei*, and *Bacteroides fragilis* showed restored counts similar to the control group following treatment with L-MKG/SNESNS. In contrast, harmful strains such as *Salmonella typhi*, *Bifidobacterium dentium*, *Campylobacter fetus*, *Bacteroides vulgatus*, *Klebsiella* aerogenes, and *Enterobacter cloacae* demonstrated reduced counts after L-MKG/SNESNS treatment compared to control and L-MKG conditions.

As depicted in Table 2, L-MKG/SNESNS had a positive effect on the following bacterial strains: *E. coli*, *Streptococcus mitis*, *Lactobacillus casei*, and *Bacteroides fragilis*.The L-MKG/SNESNS-treated rats showed restoration of normal counts of beneficial bacteria, which were similar to those of the control group. Conversely, L-MKG/SNESNS markedly decreased the count of harmful bacterial strains such as *Salmonella typhi*, *Bifidobacterium dentium*, *Campylobacter fetus*, *Bacteroides vulgatus*, *Klebsiella* aerogenes, and *Enterobacter cloacae*.The effect of L-MKG/SNESNS appeared more pronounced than that of L-MKG, potentially due to the presence of licorice extract. Previous studies have shown licorice extract to have anti-inflammatory, antioxidative stress, and immunomodulatory effects, as well as an impact on microbiota homeostasis [90].

Figure 6A:
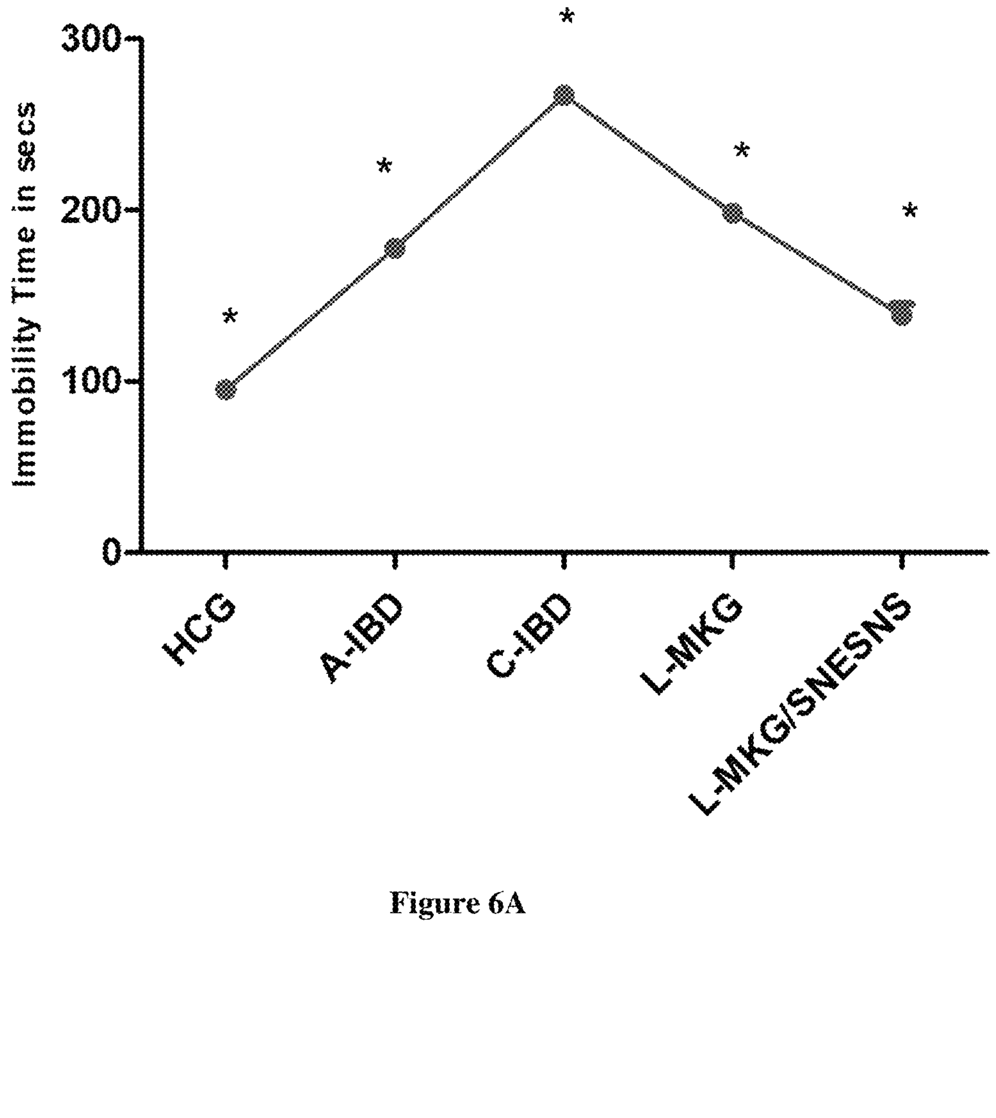
FIGS. 6A-6B illustrate the effect of Formulated L-MKG Administration on Alleviating Depression, Anxiety-like Behavior, and Spatial Memory Dysfunction in an IBD-DSS Induced Rat Model. Panels show (FIG. 6A) Tail Suspension Test (TST) and (FIG. 6B) Y maze represented as spontaneous alternation percentage (SAP). Values are expressed as Mean±S.E. (n=6 rats per group). Groups marked with the same asterisk indicate significance (*p<0.05). Groups abbreviations: HCG (Healthy Control Group), A-IBD (Acute Inflammatory Bowel Disease), C-IBD (Chronic Inflammatory Bowel Disease), L-MKG (lyophilized milk kefir), and L-MKG/SNESNS (lyophilized milk kefir as solid carriers loaded with self-nanoemulsifying self-nanosuspension).
Figure 6B:
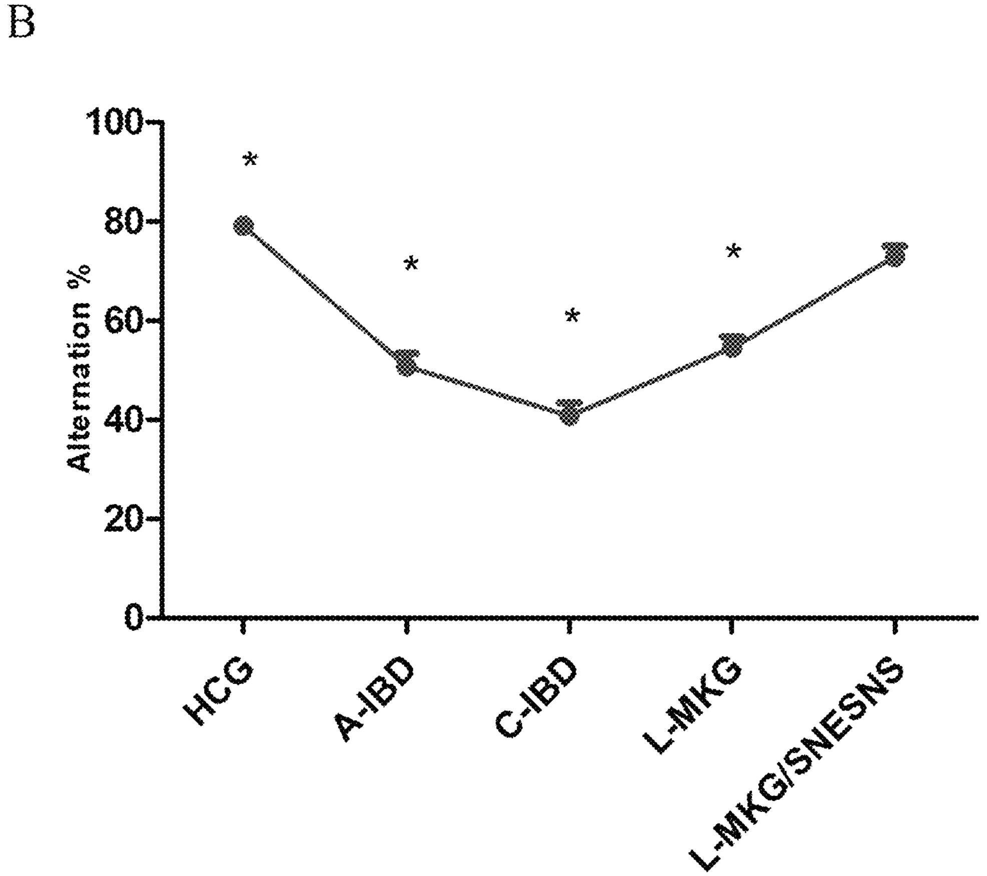

Impact of Gut-Brain Disorders on Spatial Memory Dysfunctions and Anxiety-Like Behaviors 643 in an IBD-Like Model Treated With L-MKG/SNESNS The induction of both acute and chronic IBD models reduced both spatial and cognitive memory dysfunctions significantly compared to those in the control group ($P<0.05$, FIG. 6). However, the decrease in memory recognition in chronic-IBD animals was significantly alleviated by the administration of both L-MKG and L-MKG/SNESNS compared to that in the control group and C-IBD-like model, with a more substantial improvement observed upon daily administration of L-MKG/SNESNS ($P<0.05$), as illustrated in FIG. 6B.

Additionally, a tail suspension test (TST) was conducted to assess whether the IBD model induced anxiety and depression-like behaviors in both the acute and chronic groups. The results revealed that both the acute and chronic IBD-induced models displayed poor performance in the TST, especially in the chronically induced groups, compared with the control groups (P<0.05). Conversely, a more pronounced reduction in immobility time was observed in both groups 4 and 5, with a greater decrease in immobility time among the group of rats administered our formulated L-MKG/SNESNS than among the control groups, as illustrated in FIG. 6A.

Figure 7A:
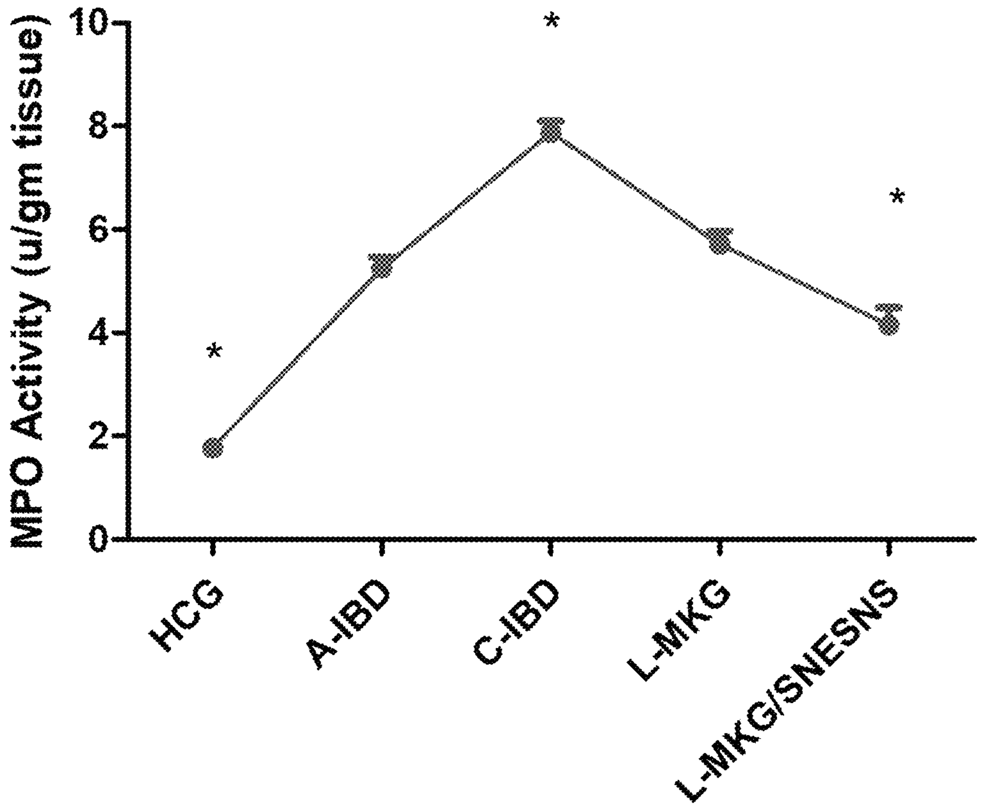
FIGS. 7A-7B illustrate the effect of Formulated L-MKG Administration on Colon MPO Activity and 5-HT Levels in the Serum and Brain in an IBD-DSS Induced Rat Model. Panels show (FIG. 7A) MPO activity and (FIG. 7B) 5-HT levels. Values are expressed as Mean±S.E. (n=6rats per group). Groups marked with the same asterisk indicate significance (*p<0.05). Groups abbreviations: HCG (Healthy Control Group), A-IBD (Acute Inflammatory Bowel Disease), C-IBD (Chronic Inflammatory Bowel Disease), L-MKG (lyophilized milk kefir), and L-MKG/SNESNS (lyophilized milk kefir as solid carriers loaded with self-nanoemulsifying self-nanosuspension).

Effect on Neurotransmitter Levels and Neurotrophic Factors in an IBD Rat-Like Model Triggered myeloperoxidase (MPO) activity was utilized to assess the extent of neutrophil granulocyte infiltration within affected tissues, specifically colon tissue. The results indicated a significant increase in MPO activity in the IBD-like model group compared with the control group, as illustrated in FIG. 7A. Conversely, a notable reduction in MPO activity was observed in both treated groups (groups 4 and 5), with a more efficient reduction noted in the group of IBD rats receiving L-MKG/SNESNS (P<0.05).

Figure 7B:
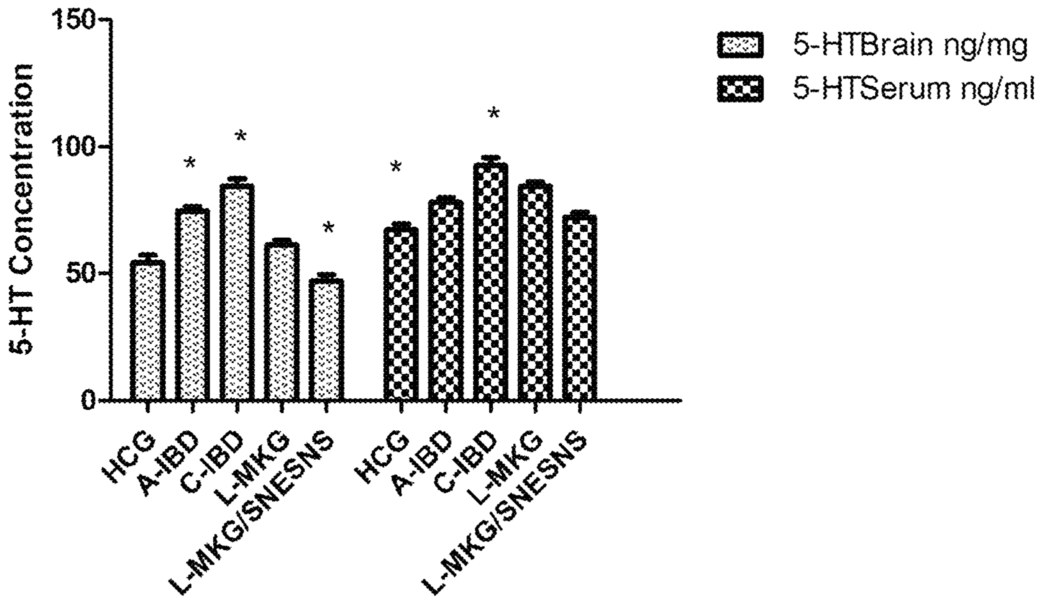
Figure 8A:
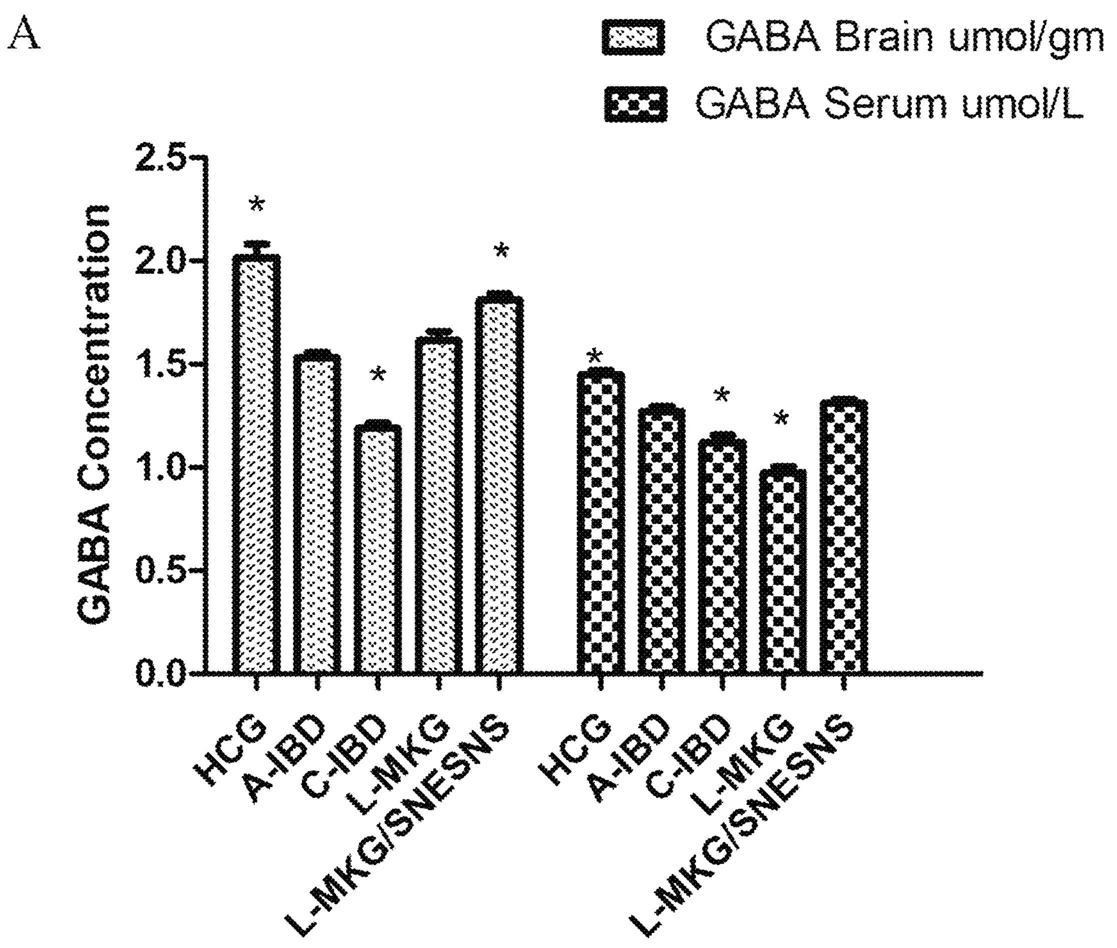
FIGS. 8A-8D illustrate the effect of Formulated L-MKG Administration on Neurotransmitter and Neurotrophic Factor Levels in the Serum and Brain in an IBD-DSS Induced Rat Model. Panels show (FIG. 8A) GABA, (FIG. 8B) DOPA, (FIG. 8C) ACH, and (FIG. 8D) BDNF levels. Values are expressed as Mean±S.E. (n=6 rats per group). Groups marked with the same asterisk indicate significance (*p<0.05). Groups abbreviations: HCG (Healthy Control Group), A-IBD (Acute Inflammatory Bowel Disease), C-IBD (Chronic Inflammatory Bowel Disease), L-MKG (lyophilized milk kefir), and L-MKG/SNESNS (lyophilized milk kefir as solid carriers loaded with self-nanoemulsifying self-nanosuspension).
Figure 8B:
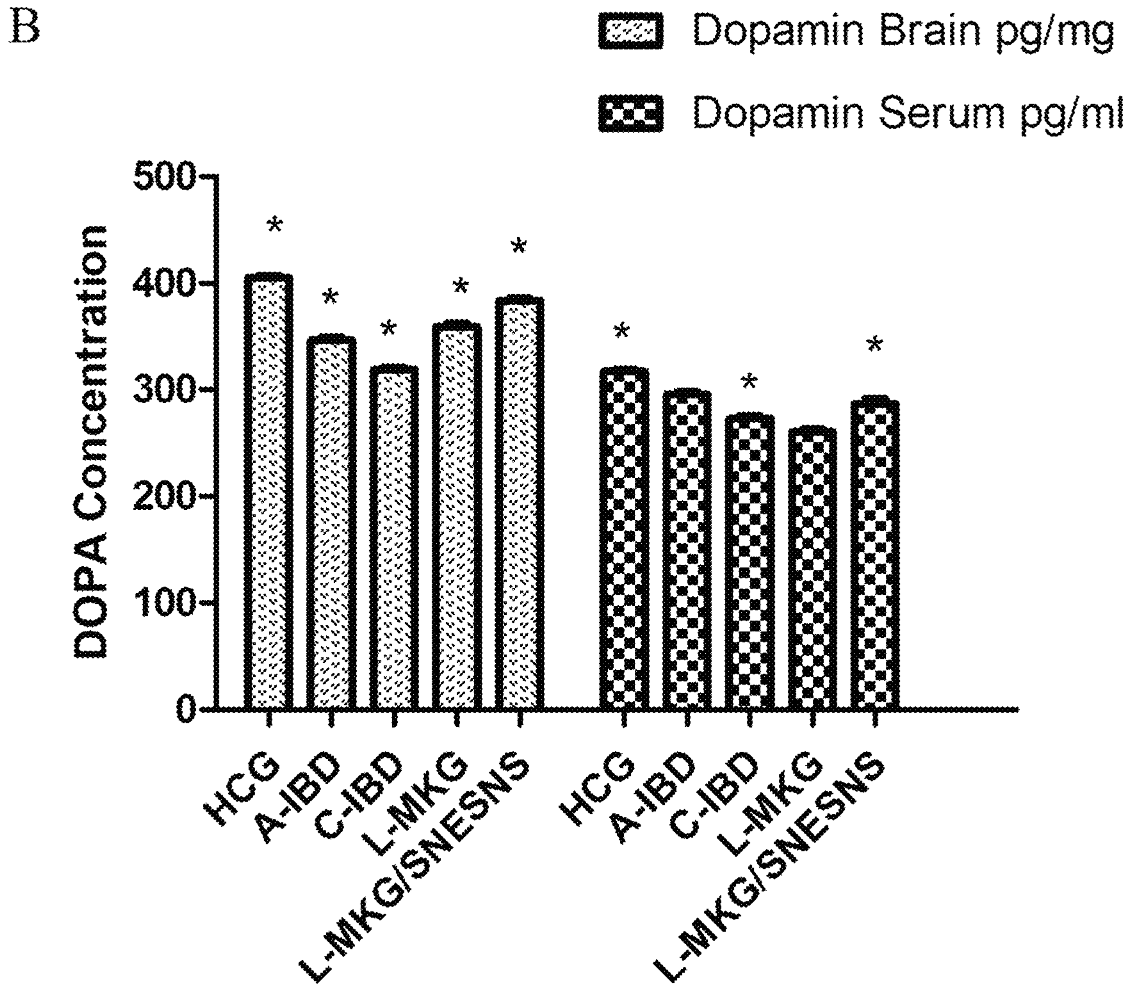
Figure 8C:
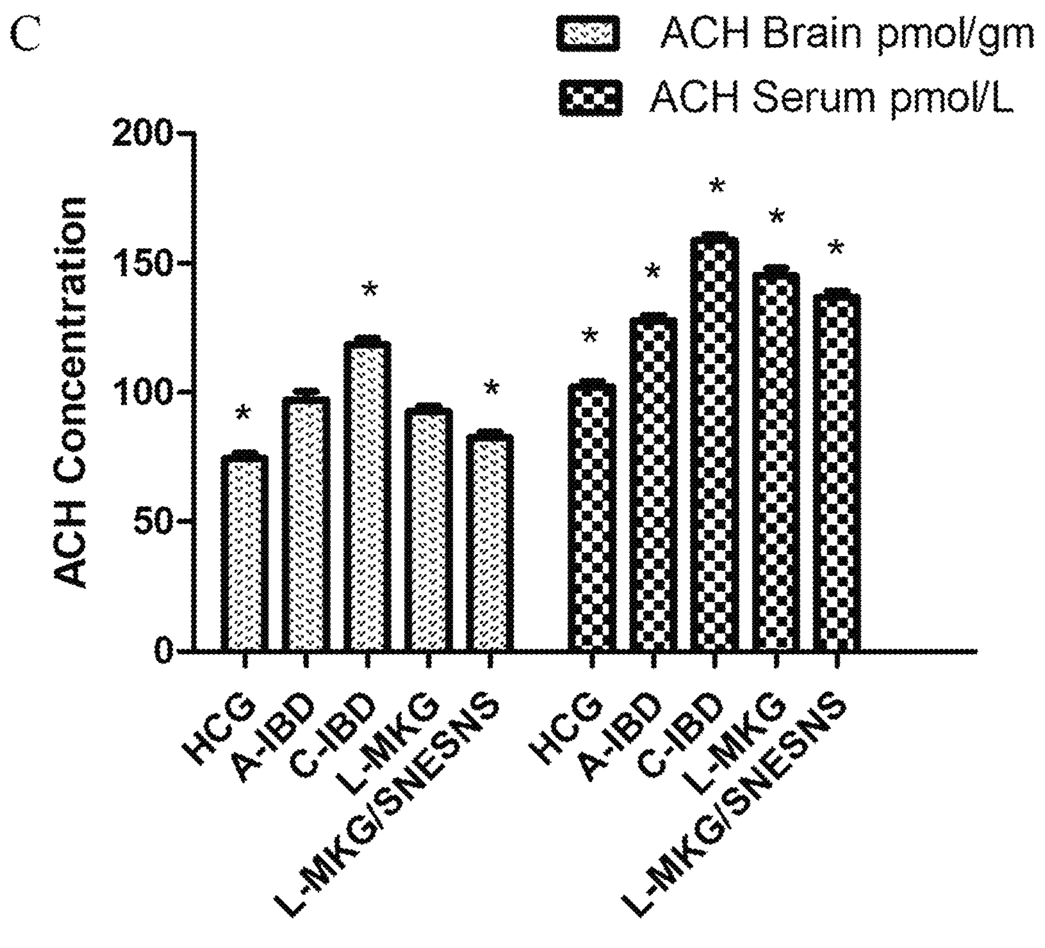
Figure 8D:
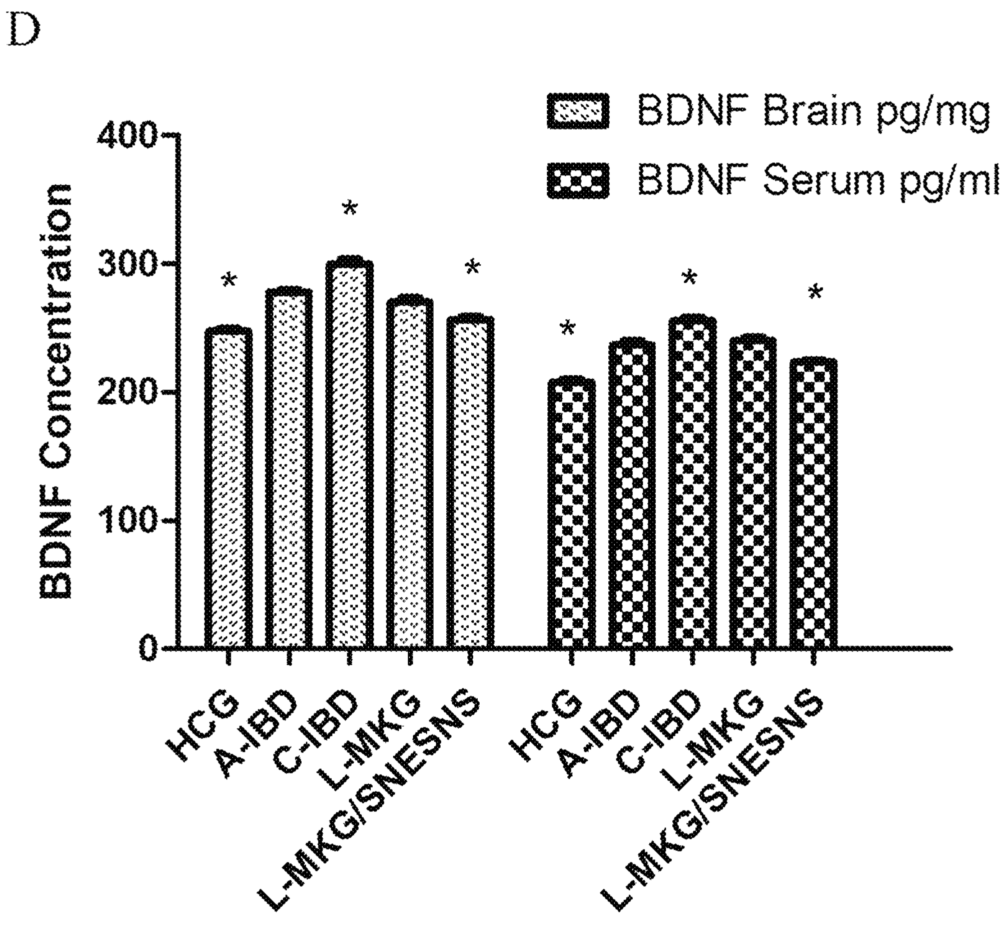
Figure 9A:
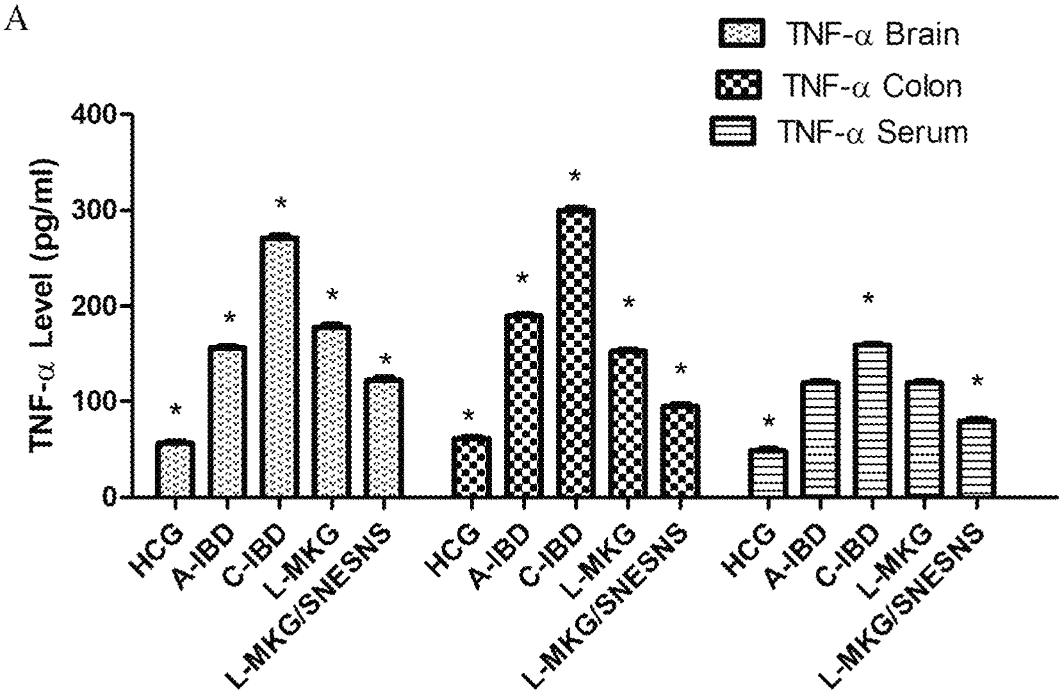
FIGS. 9A-9E illustrate the effect of formulated L-MKG administration on triggered LPS serum levels, proinflammatory cytokines and intestinal permeability in brain, colon and serum in IBD-DSS induced rat model. TNF-α (FIG. 9A), IL-B (FIG. 9B), IL6 (FIG. 9C), IL-10 (FIG. 9D), LPS serum level (FIG. 9E). Values are expressed as Mean±S.E. (n=6 rats per group). Groups marked with the same asterisk indicate significance (*p<0.05). Groups abbreviations: HCG (Healthy Control Group), A-IBD (Acute Inflammatory Bowel Disease), C-IBD (Chronic Inflammatory Bowel Disease), L-MKG (lyophilized milk kefir), and L-MKG/SNESNS (lyophilized milk kefir as solid carriers loaded with self-nanoemulsifying self-nanosuspension).
Figure 9B:
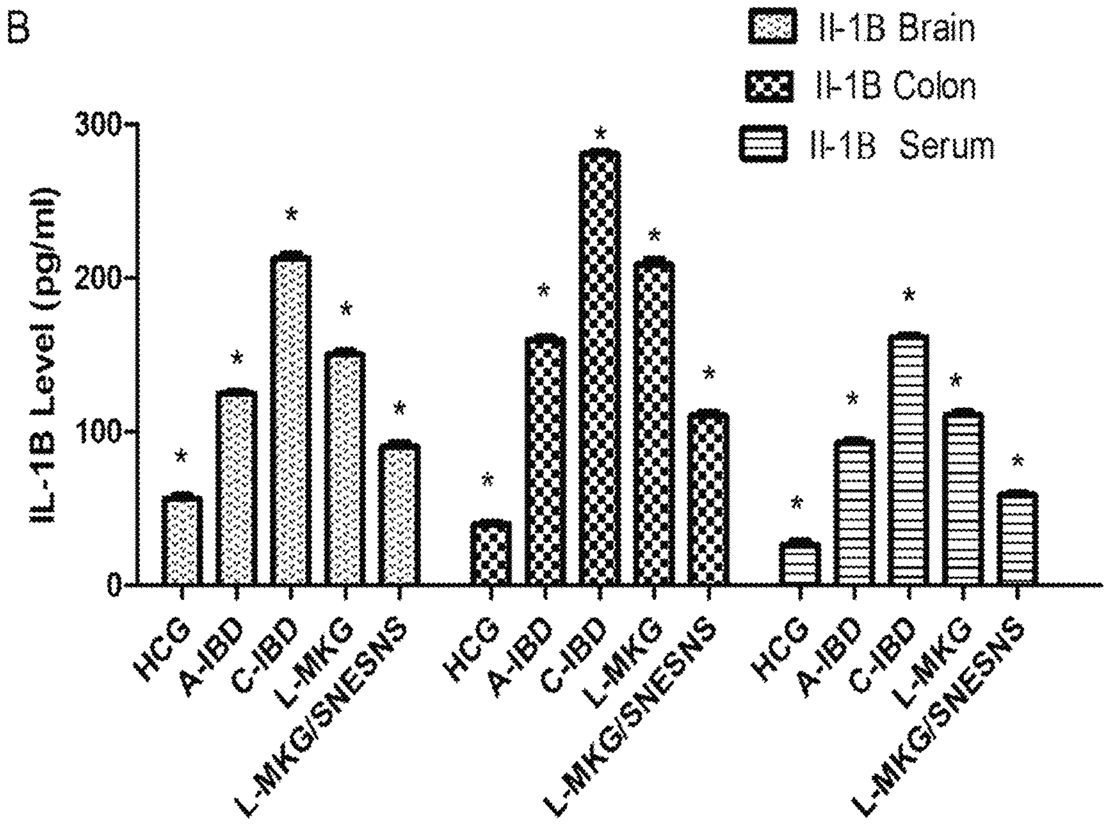
Figure 9C:
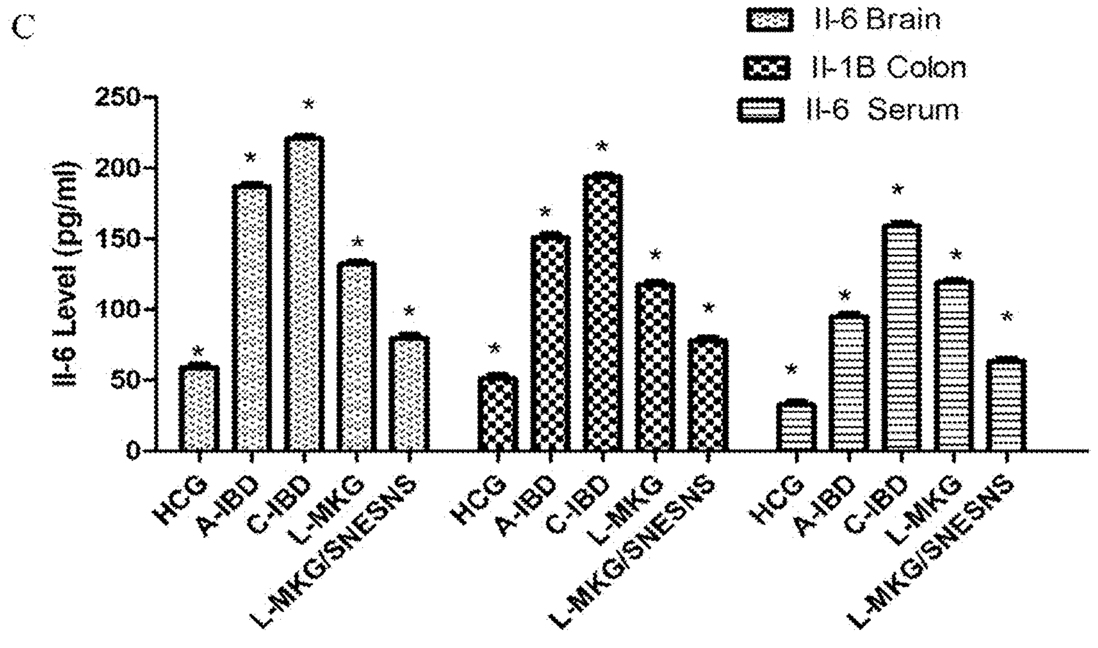
Figure 9D:
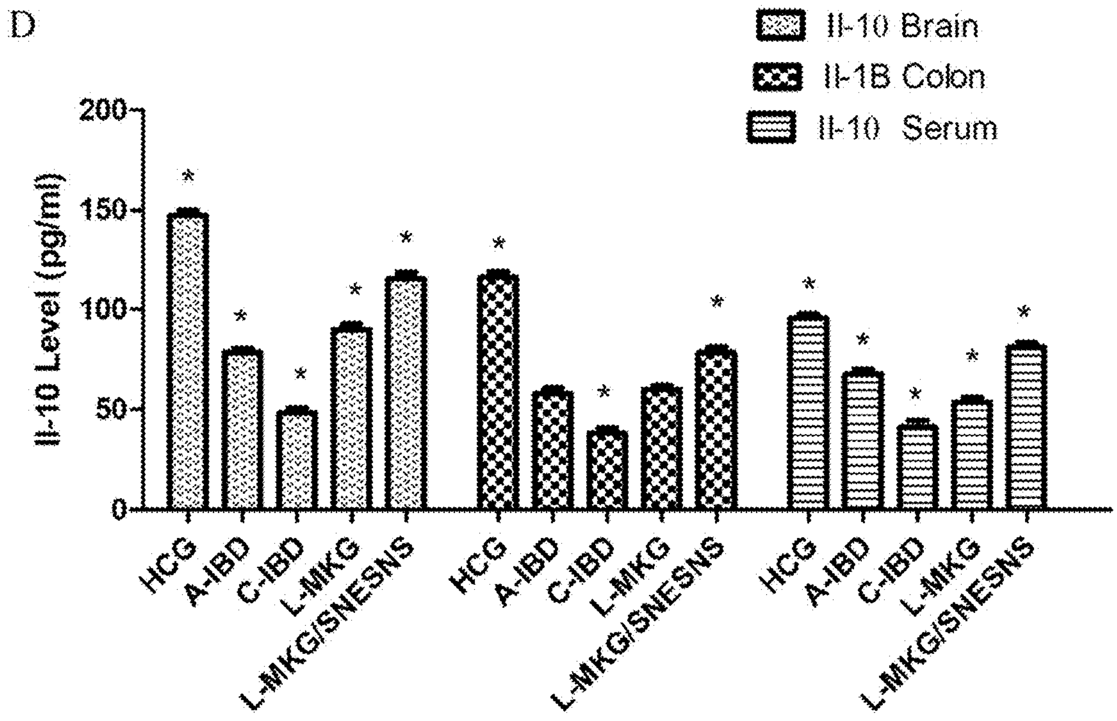
Figure 9E:
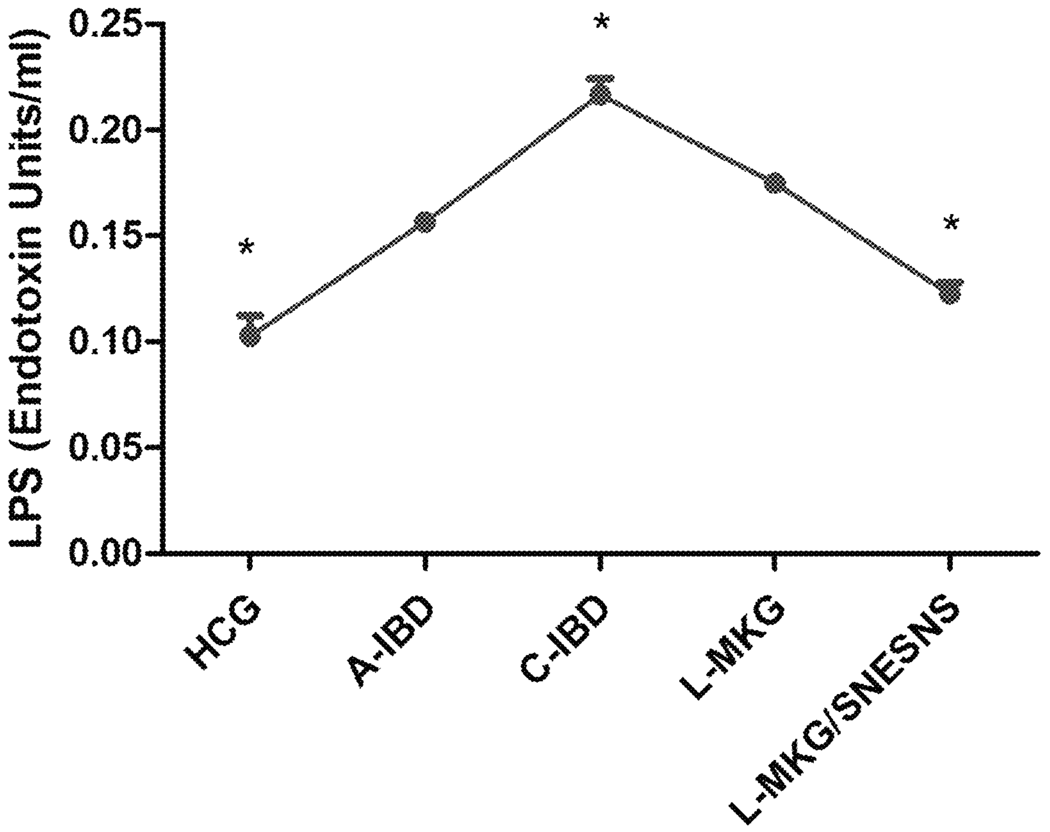

Simultaneously, 5-hydroxytryptamine (5-HT) was measured as an indicator of direct inflammatory cell activation, revealing elevated levels in the brain and serum. Daily administration of both L-MKG and L-MKG/SNESNS successfully reversed the increase in 5-HT levels, with a more pronounced restorative effect observed in group 5 than in the control group, as depicted in FIG. 7B (P<0.05). The observed crosstalk in both the brain and serum implies that lyophilized milk kefir formulations potentially influence gut-brain axis disorders in IBD-like rat models. Given the crucial role of 5-HT in neurotransmission, including its involvement in mood regulation, anxiety, sleep, appetite, and gastrointestinal function, this led us to further assess the levels of other neurotransmitters. By examining these additional neurochemical changes, we aim to gain a comprehensive understanding of the treatment's impact on the gut-brain axis compared to the control and C-IBD-like model. Effect on neurotransmitter levels and neurotrophic factors in an IBD rat-like model.

Changes in brain levels of GABA, dopamine (DA), acetylcholine (Ach), and brain-derived neurotrophic factor (BDNF), which are markers of anxiety, depression, and behavioral dysfunctions, were observed after DSS-induction of IBD-like condition. As depicted in FIGS. 8A-D, compared to those in the healthy control group (HCG), various neurotransmitters, such as GABA and dopamine, exhibited reduced levels in both the acute and chronic IBD-like models (P<0.05). Conversely, the levels of ACH and BDNF in both the brain and serum were greater in both the 705 acute and chronic IBD groups than in the control group.

Upon the administration of both L-MKG and L-MKG/SNESNS, the levels of GABA, DA, Ach, and BDNF were restored compared with those in the normal control group (P<0.05) in both the acute and chronic IBD-like models. A more effective restoration effect was observed in the L-MKG/SNESNS group 5, as illustrated in the FIGS. 8A-D. This suggests that the lyophilized milk kefir grain, especially the SNESNS formulation, has a pronounced positive impact on restoring neurotransmitter levels and neurotrophic factors in the IBD rat-like model.

The Alleviating Effect of Formulated Lyophilized Milk Kefir Grain on Triggered Proinflammatory Cytokines and Intestinal Permeability in an IBD-Like Model Proinflammatory cascades, including the levels of TNF-α, IL-6, IL-1B, and IL-10, were assessed in the brain, serum, and colon, while lipopolysaccharide (LPS) levels were measured in the serum, as shown in FIGS. 9A-E. This evaluation highlights the inflammatory response in different tissues and the systemic presence of LPS, reflecting the inflammatory status and its potential impact on the gut-brain axis. In the IBD-like model, the serum levels of TNF-α, IL-6, and IL-1B were significantly elevated in both the acute and chronic stages compared to those in the control group (P<0.05). Additionally, compared with those in the control group, LPS serum levels were increased, indicating microbiota dysbiosis, gut-brain microbiota disorders, and intestinal inflammation (P<0.05). These results collectively highlighted damage and injury to the intestinal barrier in IBD-like model rats. However, daily administration of L-MKG in group 4 and L-MKG/SNESNS in group 5 reversed this damage by modulating abnormal levels of TNF-α, IL-6, IL-1B, and IL-10 in the isolated brain, intestine, and colon tissues, as well as LPS serum levels, compared with those in the healthy control group (P<0.05). This suggests the efficiency of L-MKG, especially the SNESNS formulation, in alleviating the drawbacks associated with IBD.

Figure 10A:
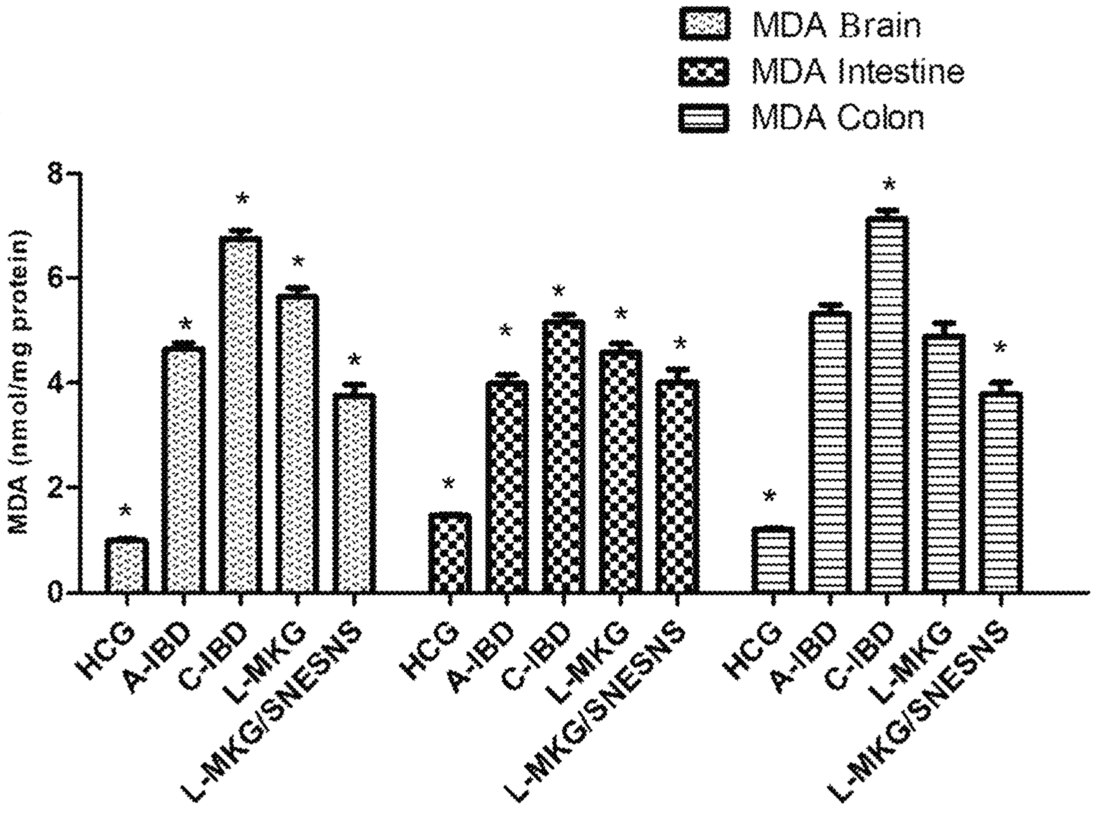
FIGS. 10A-10D illustrate the effect of formulated L-MKG administration on oxidative stress and antioxidants in the brain, colon, and serum of DSS-induced IBD rat model. MDA (FIG. 10A), NO (FIG. 10B), SOD (FIG. 10C), GST (FIG. 10D). Values are expressed as Mean±S.E (n=6 rats per group). Groups marked with the same asterisk indicate significance (*p<0.05). Groups abbreviations: HCG (Healthy Control Group), A-IBD (Acute Inflammatory Bowel Disease), C-IBD (Chronic Inflammatory Bowel Disease), L-MKG (lyophilized milk kefir), and L-MKG/SNESNS (lyophilized milk kefir as solid carriers loaded with self-nanoemulsifying self-nanosuspension).
Figure 10B:
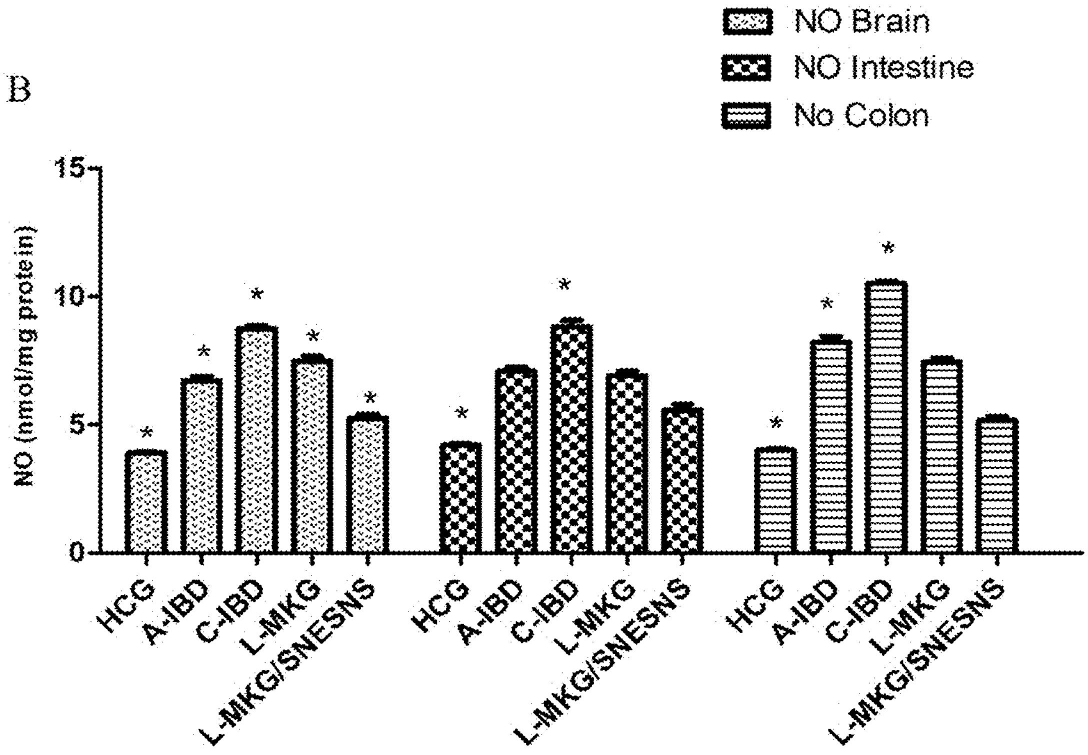
Figure 10C:
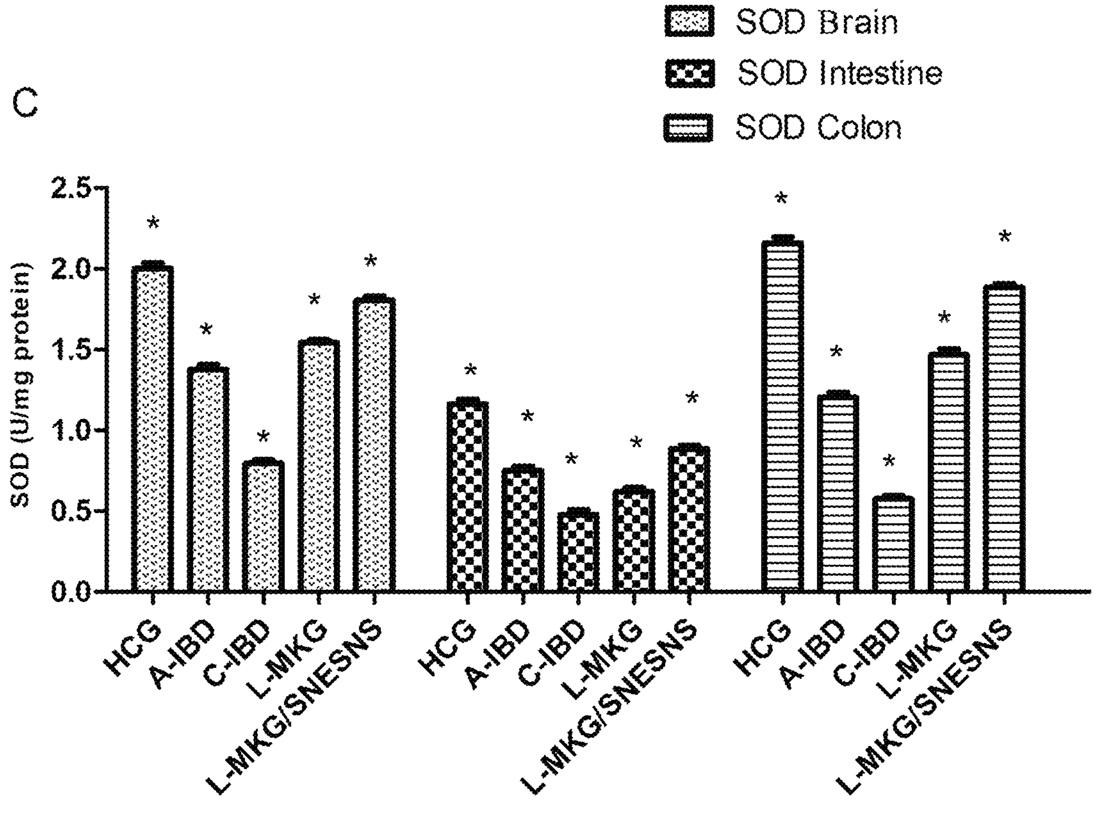
Figure 10D:
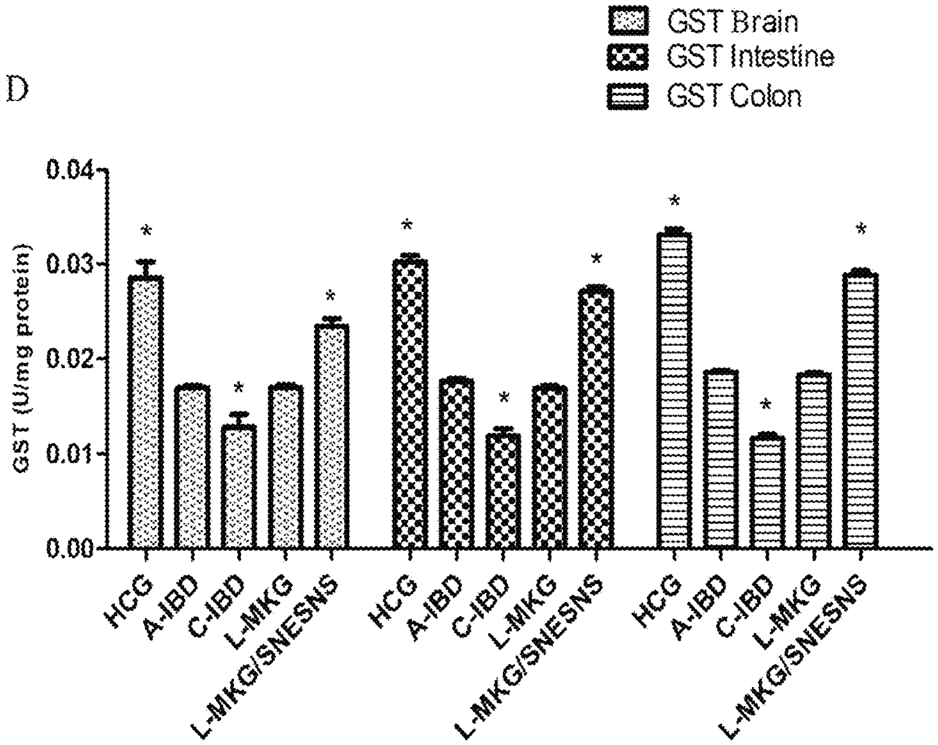

The Impact of L-MKG/SNESNS on Oxidative Stress and Antioxidant Markers in the Brain, Intestine, and Colon in an IBD-Like Model Both acute and chronic nontreated IBD-like models exhibited elevated levels of MDA, SOD, and NO in the brain, intestine, and colon, accompanied by a reduction in GST levels, as illustrated in FIGS. 10A-D. In the colon, daily administration of L-MKG, whether it was loaded with SNESNS (group 5) or only L-MKG, significantly restored the MDA, SOD, and NO levels but with a more pronounced observed effects following the daily administration of L-MKG/SNESNS, compared with those in the healthy control group (P<0.05). This restoration was associated with an increase in GST levels, surpassing the control level, as depicted in FIG. 10D.

Figure 11:
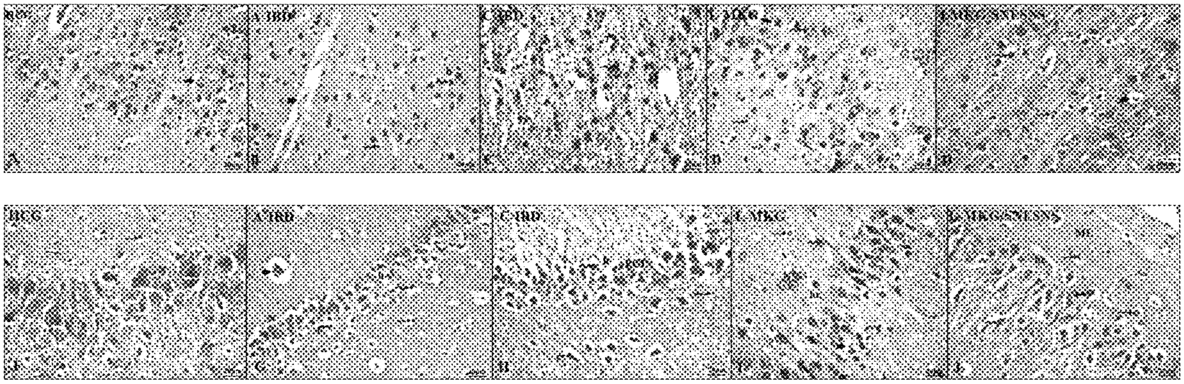
FIG. 11 illustrates the histopathological representation of cortex, and hippocampus (50×), following the administration of formulated L-MKG in IBD-DSS induced rat model. Make sure that these images are NOT stretched out. If they are, please replace with untouched originals. (Microglial cells=Zigzag arrow, Congested blood vessel=Bifid arrow, Blood vessel=Bold arrow, Pyknotic neuron=Wavy arrow, Chrunken neuron=Curved arrow, Neuropil vacuolation=V, Granule cell layer=GCL, Pericellular haloes=h, Nuclei=N).

L-MKG/SNESNS Mitigated Induced Inflammation, Damage, and Injuries in 784 Histopathological Studies of the Intestine, Stomach, and Brain As shown in FIG. 11, H&E staining revealed notable differences in the hippocampal and cortical brain structures among the HCG, A-IBD, and C-IBD groups. The HCG (group 1) exhibited normal histological patterns with clear long dendrites, typical neurons in a monomorphic pattern, well-formed microglia, and normal pyramidal cell structures in the cortex and hippocampus. In contrast, the A-IBD group displayed pathological brain damage, including dilated and congested blood vessels, dark nuclei with pericellular halos, and pyknotic nuclei. Hippocampal pyramidal neurons exhibited disorganization and major pyknotic nuclei. The C-IBD group showed even more severe neuropil vacuolation, fewer neurons, and darker stained nuclei, as well as more disturbances in the prefrontal cortex layers. However, the administration of both L-MKG and L-MKG/SNESNS reversed the observed brain injuries across different brain regions. Compared with those in group 3, the ability of SNESNS to modulate this damage was greater, with an observed improvements in group 4 (L-MKG+C-IBD). The cerebral cortex neurons appeared in a normal standard form with scattered dilated blood vessels. The hippocampal structures showed minor normally shaped neurons and pyramidal cell bodies. The most pronounced effects were observed in the L-MKG/SNESNS treatment group 5, where intact neurons with minimal pathological changes were detected. The pia matter displayed regular attachment to the prefrontal cortex, and most cell bodies appeared normal, with a border of basophilic cytoplasm and open-face nuclei. The neuropil contained glial cells with regular blood capillaries, emphasizing the highly intact and organized nature of the hippocampal structures.

Figure 12:
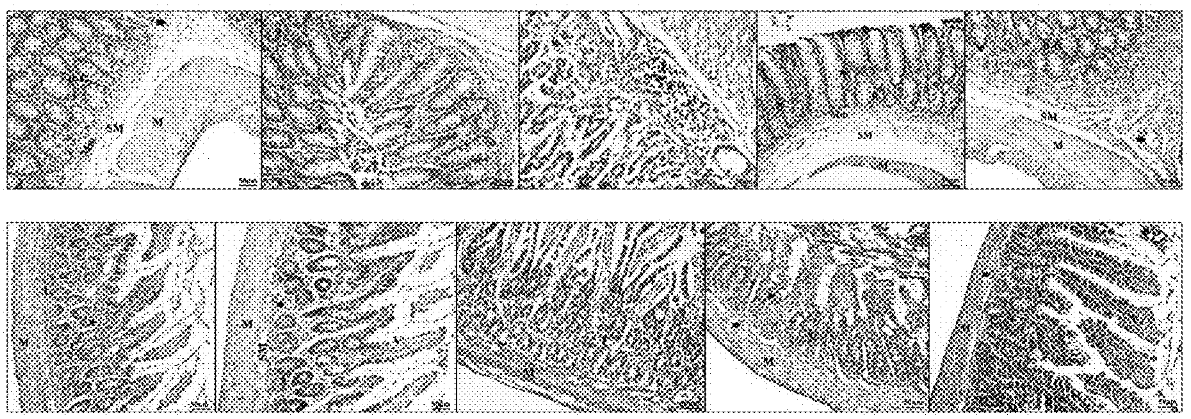
FIG. 12 illustrates histopathological representation of stomach, and intestine (50×) following the administration of formulated L-MKG in IBD-DSS induced rat model. (Mucosa (Mm), submucosa (SM), muscularis externa (M), serosa(S), villi (V), srypts region (C), congested blood vessel (bold arrow), glands (G), lamina propria (L), sunmucosa (SM) and muscularis externa (M), vertical to the fundic glands (arrows). isthmus (I), neck (N), and base (B), dilated blood vessels (bold arrow), mononuclear cell infiltrations (wavy arrow), desquamated surface mucosal cells (curved arrow), pyknotic nuclei (zizag arrow), cytoplasmic vacuolation in various glandular cells (bifid arrow), dilated gastric glands (D), Goblet cell metaplasia (arrowhead).

Microscopic examination of the intestinal and stomach sections was also conducted for all groups, as illustrated in FIG. 12. In the HCG group, the intestine displayed no histopathological alterations, exhibiting a normal structure of the mucosa (Mm), submucosa (SM), muscularis externa (M), and serosa(S). The stomach's light microscopic findings revealed regularly arranged, tightly packed tubular fundic glands (G), lamina propria (L), submucosa (SM), and muscularis externa (M). The luminal epithelium linings appeared thin, long, regular, and vertical to the fundic glands. Compared with that in the control group, the acute induction of IBD in group 2 resulted in intestinal damage, including degenerated epithelial cells lining the villi (v) and a deteriorated crypt region (C). Congested blood vessels (bold arrow) were also observed. The stomach sections of A-IBD patients exhibited degenerated cell structures, pyknotic nuclei (zigzag arrow), and mononuclear cells. Severe pathological damage and alterations were observed in the intestinal and stomach tissues of C-IBD patients, including a distorted mucosal architecture, hyperplasia of the columnar epithelium lining the villi, atrophied villi with major degenerative changes, sloughing of necrotic villi, and loss of villi (star). The daily administration of L-MKG and L-MKG/SNESNS resulted in significant improvements in the previously damaged intestinal and stomach tissues. Compared with the C-IBD group, the L-MKG group showed a relative rate of improvement in the intestine, with organized structures and little degree of degeneration. The villi structure and crypts of the intestinal gland appeared to be intact. Moreover, substantial improvement was detected in the stomach of the LMKG group (group 4) compared to that of group 3, with a slight normal intact structure of fundic glands (G), submucosa (SM), and muscularis (M). Compared with those in the HCG group, the microscopic structures of the stomach and intestine in the L-MKG/SNESNS group 5 were more intact. A clear lumen was observed, and the intestinal villi tended to preserve their natural shape. The stomach exhibited an intact structure with no dilated blood vessels or mononuclear cell infiltrations.

Figure 13:
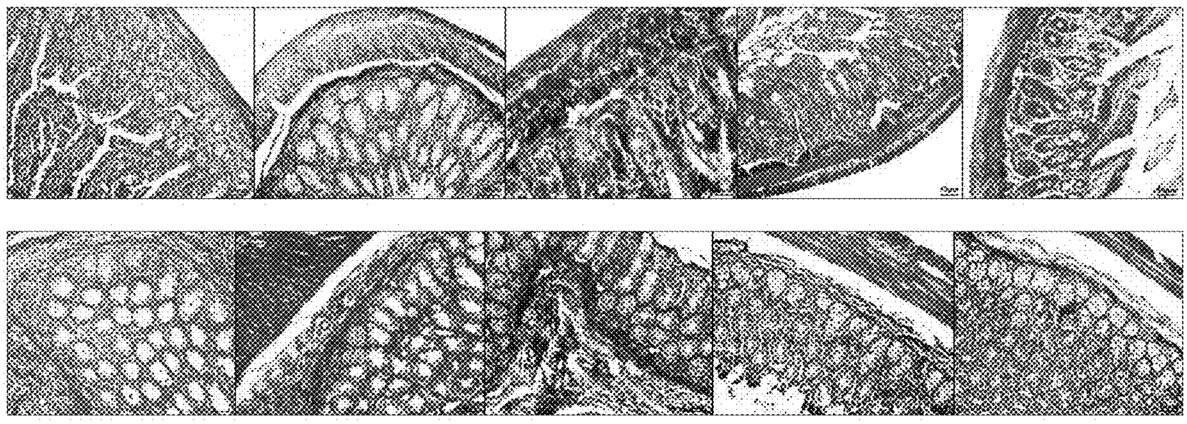
FIG. 13 illustrates representative tissue sections of stomach and intestine stained with Masson's trichrome staining illustrating the effect of formulated L-MKG administration on increased deposits of collagen in IBD-DSS induced rat model Masson's trichrome blue staining demonstrates the degree of collagen deposits in the stomach and intestine of IBD-DSS induced rat model (50×).

To assess the degree of inflammation and infiltration among all groups, Masson's trichrome staining was used to analyze collagen production. The staining type revealed increased collagen deposition in the stomach and intestine, both under chronic and acute conditions, with more prominent deposits compared to those in the control group. The degree of collagen deposition increased as the disease progressed, as indicated by the % area content of collagen fibers in FIG. 13. In contrast, compared with those in the control group, Masson's trichrome staining revealed more normal structures in the intestine and stomach, particularly in group 5, than in group 4. This observation was further supported by the calculated % mean area of collagen fibers in both treated groups in FIG. 13.

SELECTED EMBODIMENTS

Embodiment 1. A composition for self-nanoemulsifying drug delivery, comprising an oil, a surfactant, one or more active bioactive components, and a co-emulsifier or solubilizer, to spontaneously form an oil-in-water nanoemulsion.

Embodiment 2. The composition of embodiment 1, wherein the composition further comprises lyophilized milk kefir grains as a solid carrier for bioactive compounds.

Embodiment 3. The composition of any of the preceding embodiments, wherein the oil-in-water nanoemulsion has a size of up to about 200 nm upon dilution with water under gentle stirring.

Embodiment 4. A method for self-nanoemulsifying lyophilized milk kefir, comprising:

(a) obtaining milk kefir grain starters;
(b) adding the milk kefir grain starters to fully pasteurized milk';
(c) fermenting the milk at about 25° C. for about 24 hours;
(d) filtering the milk through a sterile plastic sieve;
(e) optionally storing the starter of the processed milk kefir grains under vacuum conditions at about 1 Pa and at a temperature of about −39° C. until needed for further use;
(f) lyophilizing the milk kefir grain (L-MKG) using a freeze-dryer and optionally storing the lyophilized grains until needed for further use;
(g) utilizing a ternary phase diagram for optimizing a ratio of formulation ingredients used for preparing a self-nano emulsifying system (SNES);
(h) obtaining a self-nanoemulsifying formulation selected by utilizing the ternary phase diagram;
(i) mixing Caraway oil, Tween 20, and propylene glycol in a formulation selected utilizing the ternary phase diagram;
(j) adding licorice extract;
(k) mixing with a homogenizer for about 5 min to obtain a licorice-self-nanoemulsifying self-nanosuspension (SNESNS);
(l) adding the licorice-SNESNS dropwise to the milk kefir grains (L-MKGs) to obtain a homogenous dispersion; f
(m) lyophilizing the dispersion under reduced pressure to obtain lyophilized milk kefir as solid carriers loaded with self-nanoemulsifying self-nanosuspension (L-MKG/SNESNS) in powder form.

Embodiment 5. The method of embodiment 4, wherein the grains are thoroughly washed with pasteurized milk before each new inoculation.

Embodiment 6. The method of any of the preceding embodiments, wherein the formulation selected utilizing the ternary phase diagram is selected from the group consisting of about 30% Caraway oil, about 60% Tween 20, and about 10% propylene glycole (w/w).

Embodiment 7. The method of claim 6, wherein licorice extract is added to the formulation to obtain a final formulation having a concentration of about 3 mg/mL.

Embodiment 8. The method of claim 6, wherein the final Tween 20 concentration should be greater or equal to about 40%.

Embodiment 9. The method of any of the preceding embodiments, wherein a symbiotic mixture of microorganisms in kefir comprises bacterial strains *E. coli*, *Streptococcus mitis*, *Lactobacillus casei*, *Bacteroides fragilis*, or mixtures thereof.

Embodiment 10. The method of any of the preceding embodiments, wherein the self-nanosuspension is used for the delivery of bioactive components to selectively target highly inflamed intestinal mucosa.

Embodiment 11. The method of any of the preceding embodiments, wherein the combination of nanotechnology-based formulations and the use of kefir grains as a solid carrier for bioactive agents is a dual-phase delivery system.

Embodiment 12. The method of claim 11, wherein the bioactive components delivered with the lyophilized milk kefir grains comprise licorice extract and caraway oil.

Embodiment 13. The method of claim 12, wherein the final formulation is useful for restoring neurotransmitter levels and alleviating inflammatory processes in a subject in need thereof.

Embodiment 14. The method of claim 13, wherein the final formulation is administered to the subject for improving the symptoms of chronic inflammatory bowel diseases (IBD) and for managing IBD-related cognitive decline.

REFERENCES

1. Pereira TMC, Côco LZ, Ton AMM, et al. The Emerging Scenario of the Gut-Brain Axis: 1207 The Therapeutic Actions of the New Actor Kefir against Neurodegenerative Diseases. 2021 Nov 20;10(11).
2. Albuquerque Pereira MdF, Morais de Ávila LG, Ávila Alpino GdC, et al. Milk kefir alters 1210 fecal microbiota impacting gut and brain health in mice. Applied Microbiology and Biotechnology. 2023 2023/08/01; 107(16):5161-5178.
3. Zhang H, Zhang Z, Liao Y, et al. The Complex Link and Disease Between the Gut Microbiome and the Immune System in Infants [Review]. Frontiers in cellular and infection microbiology. 2022 2022-June-15;12. [3] Nair, A.B., Jacob S. (2016). A simple practical guide for dose conversion between animal and human. J Basic Clin Pharma 2016, 7:27-31.
4. Hong Z, Piao M. Effect of Quercetin Monoglycosides on Oxidative Stress and Gut 1216 Microbiota Diversity in Mice with Dextran Sodium Sulphate-Induced Colitis. Biomed Res Int. 2018 2018/11/12;2018:8343052.
5. Li H, Chen X, Liu J, et al. Ethanol extract of *Centella asiatica* alleviated dextran sulfate 1219 sodium-induced colitis: Restoration on mucosa barrier and gut microbiota homeostasis. J Ethnopharmacol. 2021 Mar 1;267:113445.
6. Anwar MM, Pérez-Martínez L, Pedraza-Alva G. Exploring the Significance of Microglial 1222 Phenotypes and Morphological Diversity in Neuroinflammation and Neurodegenerative 1223 Diseases: From Mechanisms to Potential Therapeutic Targets. Immunological Investigations.1-56.
7. Zhao Ma, Chu J, Feng S, et al. Immunological mechanisms of inflammatory diseases caused by gut microbiota dysbiosis: A review. Biomedicine & Pharmacotherapy. 2023 2023/08/01/;164:114985.
8. Peruhova M, Miteva D, Kokudeva M, et al. Cytokine Signatures in Inflamed Mucosa of 1229 IBD Patients: State-of-the-Art. Gastroenterology Insights. 2024;15 (2):471-485.
9. Koyama Y, Kobayashi Y, Hirota I, et al. A new therapy against ulcerative colitis via the 1231 intestine and brain using the Si-based agent. Scientific reports. 2022 1232 2022/06/10;12(1):9634.
10. Di Vincenzo F, Del Gaudio A, Petito V, et al. Gut microbiota, intestinal permeability, and 1234 systemic inflammation: a narrative review. Internal and Emergency Medicine. 2024 2024/03/01;19(2):275-293.
11. Günther C, Rothhammer V, Karow M, et al. The Gut-Brain Axis in Inflammatory Bowel 1237 Disease—Current and Future Perspectives. International Journal of Molecular Sciences. 2021;22(16):8870.
12. Dash S, Syed YA, Khan MR. Understanding the Role of the Gut Microbiome in Brain 1240 Development and Its Association With Neurodevelopmental Psychiatric Disorders. Front 1241 Cell Dev Biol. 2022;10:880544.
13. Lee HL, Kim JM. Anti-Amnesic Effect of Synbiotic Supplementation Containing *Corni* 1243 *fructus* and *Limosilactobacillus reuteri* in DSS-Induced Colitis Mice. 2022 Dec 21;24(1).
14. Emge JR, Huynh K, Miller EN, et al. Modulation of the microbiota-gut-brain axis by 1245 probiotics in a murine model of inflammatory bowel disease. American journal of 1246 physiology Gastrointestinal and liver physiology. 2016 Jun 1;310(11):G989-98.
15. Anwar MM, Özkan E, Shomalizadeh N, et al. Assessing the role of primary healthy microglia and gap junction blocker in hindering Alzheimer's disease neuroinflammatory 1249 type: Early approaches for therapeutic intervention [Original Research]. Frontiers in 1250 Neuroscience. 2023 2023-January-10;16.
16. Anwar MM, Fathi MH. Early approaches of YKL-40 as a biomarker and therapeutic target 1252 for Parkinson's disease. Neurodegenerative Disease Management. 2023.
17. Holzer P, Reichmann F, Farzi A. Neuropeptide Y, peptide YY and pancreatic polypeptide in the gut-brain axis. Neuropeptides. 2012 Dec;46(6):261-74.
18. Xiong RG, Li J, Cheng J, et al. The Role of Gut Microbiota in Anxiety, Depression, and Other Mental Disorders as Well as the Protective Effects of Dietary Components. 2023 Jul 1257 23;15(14).
19. Loh JS, Mak WQ, Tan LKS, et al. Microbiota-gut-brain axis and its therapeutic applications in neurodegenerative diseases. Signal Transduction and Targeted Therapy. 2024 2024/02/16;9(1):37.
20. Ansari F, Neshat M, Pourjafar H, et al. The role of probiotics and prebiotics in modulating of the gut-brain axis [Review]. Frontiers in Nutrition. 2023 2023-July-26;10.
21. Vitali R, Prioreschi C, Lorenzo Rebenaque L. Gut-Brain Axis: Insights from Hippocampal Neurogenesis and Brain Tumor Development in a Mouse Model of Experimental Colitis Induced by Dextran Sodium Sulfate. 2022 Sep 29;23(19).
22. Jialing L, Yangyang G, Jing Z, et al. Changes in serum inflammatory cytokine levels and intestinal flora in a self-healing dextran sodium sulfate-induced ulcerative colitis murine model. Life Sci. 2020 Dec 15;263: 118587.
23. Balasubramanian R, Schneider E, Gunnigle E, et al. Fermented foods: Harnessing their potential to modulate the microbiota-gut-brain axis for mental health. Neuroscience & Biobehavioral Reviews. 2024 2024/03/01/;158:105562.
24. Wang X, Zhang P, Zhang X. Probiotics Regulate Gut Microbiota: An Effective Method to 1288 Improve Immunity. 2021 Oct 8;26(19).
25. Bell V, Ferrão J, Pimentel L, et al. One Health, Fermented Foods, and Gut Microbiota. 1290 2018 Dec 3;7(12).
26. Peluzio MdCG, Dias MdMe, Martinez JA, et al. Kefir and Intestinal Microbiota Modulation: Implications in Human Health [Review]. Frontiers in Nutrition. 2021 2021-February-22;8.
27. Saadatzadeh A, Atyabi F, Fazeli MR, et al.. Biochemical and pathological evidences on the 1295 benefit of a new biodegradable nanoparticles of probiotic extract in murine colitis. Fundamental & clinical pharmacology. 2012 Oct;26(5):589-98.

28. Nascimento da Silva K, Fávero AG, Ribeiro W, et al. Effects of kefir fermented milk 1298 beverage on sodium dextran sulfate (DSS)-induced colitis in rats. Heliyon. 2023 Jan;9(1):e12707.
29. Albuquerque Pereira MF, Morais de Ávila LG. Milk kefir alters fecal microbiota impacting gut and brain health in mice. 2023 Aug;107(16):5161-5178.
30. Das K, Daveluy S, Kroumpouzos G. Efficacy and Toxicity of Classical Immunosuppressants, Retinoids and Biologics in Hidradenitis Suppurativa. 2022 Jan 27;11(3).
31. Agrawal H, Doan H, Pham B, et al. Systemic immunosuppressive therapies for uveitis in 1306 developing countries. Indian journal of ophthalmology. 2020 Sep; 68(9):1852-1862.
32. Rutgeerts PJ. The limitations of corticosteroid therapy in Crohn's disease. Alimentary 1308 Pharmacology & Therapeutics. 2001;15(10):1515-1525.
33. McGovern CJ, González-Orozco BD, Jiménez-Flores R. Evaluation of Kefir Grain Microbiota, Grain Viability, and Kefir Bioactivity from Fermenting Dairy Processing By-Products. Journal of Dairy Science. 2024 2024/02/17/.
34. Anwar MM, Ali OS, Rashed LA, et al. The Neuro Engraftment and Neuroregenerative 1313 effects of Hydrogen Sulphide Donor, Intracerebral MSCs, Ginko Biloba and Kefir in Attenuating Neuropathological hallmarks of Lipopolysaccharide induced Alzheimer's disease Rat models. International Journal of Aging Research. 2019 07/18;2(3):38.
35. Anwar MM, Ali OS, Rashed LA, et al. The effect of using kefir grains and mesenchymal stem cells in LPS-induced Alzheimer's disease neuroinflammatory model [Research article]. Revista eNeurobiología. 2019; 10(25):23.
36. Anwar MM, Ali OS, Rashed LA, et al. Regulation of miRNA- 124, Nuclear Factor-Kappa B and β-Catenin Expression in Response to Novel Therapeutic Protocol in LPS Induced Alzheimer's Disease in Rats [Research article]. Research in Neuroscience. 2018;7(1):17.
37. Qin H, Wu H, Shen K, et al. Fermented Minor Grain Foods: Classification, Functional 1323Components, and Probiotic Potential. Foods (Basel, Switzerland). 2022 Oct 11;11(20).
38. Ghosh P, Luthra R. Freeze Drying: A Review of Key Factors and Developments. Journal of Food Science and Technology. 54(6), 1516-1525 (2017).
39. Papalexandratou Z, et al. Lyophilization of Probiotc Bacteria: A Review. Food Control. 33(2), 352-364 (2103).
40. El-Laithy HM, Basalious EB, El-Hoseiny BM, et al. Novel self-nanoemulsifying self-nanosuspension (SNESNS) for enhancing oral bioavailability of diacerein: Simultaneous portal blood absorption and lymphatic delivery. Int J Pharm. 2015 Jul 25;490(1-2): 146-54.
41. Boseila AA, Ghareeb AZ, AbdElwahab MG, et al. Throat spray formulated with virucidal Pharmaceutical excipients as an effective early prophylactic or treatment strategy against pharyngitis post-exposure to SARS COV-2. European journal of pharmaceutics and 1377 biopharmaceutics: official journal of Arbeitsgemeinschaft fur Pharmazeutische Verfahrenstechnik eV. 2024 Apr 6:114279.
42. Balaha M, Kandeel S, Elwan W. Garlic oil inhibits dextran sodium sulfate-induced ulcerative colitis in rats. Life Sci. 2016 2016/02/01/;146:40-51.
43. Ma X, Hu Y, Li X, et al. Periplaneta americana Ameliorates Dextran Sulfate Sodium-Induced Ulcerative Colitis in Rats by Keap1/Nrf-2 Activation, Intestinal Barrier Function, and Gut Microbiota Regulation [Original Research]. Frontiers in Pharmacology. 2018 1384 2018-August-22;9.
43. Gerges SH, Tolba MF, Elsherbiny DA, et al. The natural flavonoid galangin ameliorates dextran sulphate sodium-induced ulcerative colitis in mice: Effect on Toll-like receptor 4, inflammation and oxidative stress. Basic & Clinical Pharmacology & Toxicology. 2020; 127(1):10-20.
44. Ladda B, Jantararussamee C, Pradidarcheep W, et al. Anti-Inflammatory and Gut Microbiota Modulating Effects of Probiotic *Lactobacillus paracasei* MSMC 39 -1 on Dextran Sulfate Sodium-Induced Colitis in Rats. Nutrients. 2023;15(6):1388.
65. Luang-In V, Deeseenthum S, Chunchom S, et al. Effects of kefir fermentation on 1393 antioxidation activities (in vitro) and antioxidative stress (in vivo) of different Thai rice milk varieties. Pharmacognosy Journal. 2018 07/11;10.
45. Gao X, Li B. Chemical and microbiological characteristics of kefir grains and their fermented dairy products: A review. Cogent Food & Agriculture. 2016 1397 2016/12/31;2(1):1272152.
46. Apalowo OE, Adegoye GA, Mbogori T, et al. Nutritional Characteristics, Health Impact, and Applications of Kefir. Foods (Basel, Switzerland). 2024;13(7):1026.
47. Alves E, Ntungwe EN, Gregório J, et al. Characterization of Kefir Produced in Household Conditions: Physicochemical and Nutritional Profile, and Storage Stability. Foods (Basel, Switzerland). 2021;10(5):1057.
48. Wang Z, Liang XY, Chang X, et al. MMI-0100 Ameliorates Dextran Sulfate Sodium-Induced Colitis in Mice through Targeting MK2 Pathway. Molecules (Basel, Switzerland). 2019;24(15):2832.
49. Qin L, Yao ZQ, Chang Q, et al. Swimming attenuates inflammation, oxidative stress, and apoptosis in a rat model of dextran sulfate sodium-induced chronic colitis. Oncotarget. 2017 January 31;8(5):7391-7404.
50. Wen C, Chen D, Zhong R, et al. Animal models of inflammatory bowel disease: category and evaluation indexes. Gastroenterology report. 2024;12:goae021.
51. Mashtoub S, Howarth GS. Emu Oil and zinc monoglycerolate independently reduce disease severity in a rat model of ulcerative colitis. BioMetals. 2023 2023/12/01;36(6):1331-1345.
52. Wang K, Jin X, You M, et al. Dietary Propolis Ameliorates Dextran Sulfate Sodium-Induced Colitis and Modulates the Gut Microbiota in Rats Fed a Western Diet. Nutrients. 2017 Aug 14;9(8).
53. Adamkova P, Hradicka P, Kupcova Skalnikova H, et al. Dextran Sulphate Sodium Acute Colitis Rat Model: A Suitable Tool for Advancing Our Understanding of Immune and Microbial Mechanisms in the Pathogenesis of Inflammatory Bowel Disease. Veterinary sciences. 2022;9(5):238.
54. Zhang L, Cao N, Wang Y, et al. Improvement of Oxazolone-Induced Ulcerative Colitis in Rats Using Andrographolide. Molecules (Basel, Switzerland). 2020;25(1):76.
55. Shahid M, Raish M, Ahmad A, et al. Sinapic Acid Ameliorates Acetic Acid-Induced Ulcerative Colitis in Rats by Suppressing Inflammation, Oxidative Stress, and Apoptosis. Molecules (Basel, Switzerland). 2022; 27(13):4139.

56. Bhatia A, Saikia PP, Dkhar B, et al. Anesthesia protocol for ear surgery in Wistar rats (animal research). Animal models and experimental medicine. 2022 Apr;5(2):183-188.
57. Araruna MEC, Júnior EBA, Serafim CAdL, et al. (−)-Fenchone Prevents Cysteamine-Induced Duodenal Ulcers and Accelerates Healing Promoting Re-Epithelialization of Gastric Ulcers in Rats via Antioxidant and Immunomodulatory Mechanisms. Pharmaceuticals. 2024;17(5):641.
58. Matei-Laţiu M-C, Gal A-F, Rus V, et al. Intestinal Dysbiosis in Rats: Interaction between Amoxicillin and Probiotics, a Histological and Immunohistochemical Evaluation. Nutrients. 2023;15(5):1105.
59. Farmer JJ, 3rd, Davis BR, Hickman-Brenner FW, et al. Biochemical identification of new species and biogroups of Enterobacteriaceae isolated from clinical specimens. Journal of clinical microbiology. 1985 Jan; 21(1):46-76.
60. Rath HC, Schultz M, Freitag R, et al. Different subsets of enteric bacteria induce and perpetuate experimental colitis in rats and mice. Infection and immunity. 2001 Apr;69(4):2277-85.
61. O'Hara CM, Rhoden DL, Miller JM. Reevaluation of the API 20E identification system versus conventional biochemicals for identification of members of the family Enterobacteriaceae: a new look at an old product. Journal of clinical microbiology. 1992 Jan;30(1):123-5.
62. O'Hara CM, Tenover FC, Miller JM. Parallel comparison of accuracy of API 20E, Vitek GNI, MicroScan Walk/Away Rapid ID, and Becton Dickinson Cobas Micro ID-E/NF for identification of members of the family Enterobacteriaceae and common gram-negative, non-glucose-fermenting bacilli. Journal of clinical microbiology. 1993 Dec;31(12):3165-9.
63. Gadotti VM, Andonegui G, Zhang Z, et al. Neuroimmune Responses Mediate Depression-Related Behaviors following Acute Colitis. iScience. 2019 Jun 28;16: 12-21.
64. Shi X, Bai H, Wang J, et al. Behavioral Assessment of Sensory, Motor, Emotion, and Cognition in Rodent Models of Intracerebral Hemorrhage [Review]. Front Neurol. 2021 2021-June-17;12.
65. Omeiza NA, Abdulrahim HA, Alagbonsi AI, et al. Melatonin salvages lead-induced neuro-cognitive shutdown, anxiety, and depressive-like symptoms via oxido-inflammatory and cholinergic mechanisms. Brain and Behavior. 2021;11(8):e2227.
66. Samaey C, Schreurs A, Stroobants S, et al. Early Cognitive and Behavioral Deficits in Mouse Models for Tauopathy and Alzheimer's Disease. Frontiers in aging neuroscience. 2019;11:335.
67. Sitnikova E. Behavioral and Cognitive Comorbidities in Genetic Rat Models of Absence Epilepsy (Focusing on GAERS and WAG/Rij Rats). Biomedicines. 2024; 12(1):122.
68. Ma J, Wang R, Chen Y, et al. 5-HT attenuates chronic stress-induced cognitive impairment in mice through intestinal flora disruption. J Neuroinflammation. 2023 Feb 3;20(1):23.
69. Chermat R, Thierry B, Mico J, et al. Adaptation of the tail suspension test to the rat. Journal de pharmacologie. 1986 06/01;17:348-350.
70. Ueno H, Takahashi Y, Murakami S, et al. Effect of simultaneous testing of two mice in the tail suspension test and forced swim test. Scientific reports. 2022 2022/06/02;12(1):9224.
71. Castagné V, Moser P, Roux S, et al. Rodent models of depression: forced swim and tail suspension behavioral despair tests in rats and mice. Current protocols in neuroscience. 2011 Apr;Chapter 8:Unit 8.10A.
72. Foudah AI, Alqarni MH, Alam A, et al. Rutin Improves Anxiety and Reserpine-Induced Depression in Rats. Molecules (Basel, Switzerland). 2022;27(21): 7313.
94. d'Isa R, Comi G, Leocani L. Apparatus design and behavioural testing protocol for the evaluation of spatial working memory in mice through the spontaneous alternation T-maze. Scientific reports. 2021 2021/10/27;11(1):21177.
73. Zhang Y, Zhu M, Sun Y, et al. Environmental noise degrades hippocampus-related learning and memory. Proceedings of the National Academy of Sciences. 2021;118(1):e2017841117.
74. Boon WC, Simpson ER. Chapter 33-Neuroendocrine Inherited or Induced Aromatase Enzyme Deficits. In: Fink G, Pfaff DW, Levine JE, editors. Handbook of Neuroendocrinology. San Diego: Academic Press; 2012. p. 723-737.
75. Bradley PP, Priebat DA, Christensen RD, et al. Measurement of cutaneous inflammation: estimation of neutrophil content with an enzyme marker. The Journal of investigative dermatology. 1982Mar;78(3):206-9.
76. Buege JA, Aust SD. Microsomal lipid peroxidation. Methods in enzymology. 1978;52:302-10.
77. Belguendouz L, Fremont L, Linard A. Resveratrol inhibits metal ion-dependent and independent peroxidation of porcine low-density lipoproteins. Biochem Pharmacol. 1997 May 9;53(9):1347-55.
78. Levine RL, Garland D, Oliver CN, et al. Determination of carbonyl content in oxidatively modified proteins. Methods in enzymology. 1990;186:464-78.
79. Anwar MM, Laila IMI. Mitigative effect of caffeine against diclofenac-induced hepato-renal damage and chromosomal aberrations in male albino rats. BMC complementary medicine and therapies. 2022 December 8;22(1):327.
80. Anwar MM, Laila IMI. The ameliorating effect of Rutin on hepatotoxicity and 1497 inflammation induced by the daily administration of vortioxetine in rats. BMC complementary medicine and therapies. 2024 2024/04/05;24(1):153.
81. Kakkar P, Das B, Viswanathan PN. A modified spectrophotometric assay of superoxide dismutase. Indian journal of biochemistry & biophysics. 1984 Apr;21(2): 130-2.
82. Miranda KM, Espey MG, Wink DA. A rapid, simple spectrophotometric method for simultaneous detection of nitrate and nitrite. Nitric oxide: biology and chemistry. 2001 Feb;5(1):62-71.
83. Habig WH, Pabst MJ, Jakoby WB. Glutathione S-transferases. The first enzymatic step in mercapturic acid formation. The Journal of biological chemistry. 1974 Nov 25;249(22):7130-9.
84. Khursheed R, Singh SK, Wadhwa S, et al. Exploring role of probiotics and Ganoderma lucidum extract powder as solid carriers to solidify liquid self-nanoemulsifying delivery systems loaded with curcumin. Carbohydr Polym. 2020 Dec 15;250:116996.
85. de Souza HF, Monteiro GF, Bogáz LT, et al. Bibliometric analysis of water kefir and milk kefir in probiotic foods from 2013 to 2022: A critical review of recent applications and prospects. Food Research International. 2024 2024/01/01/;175:113716.

86. Xu Z, Shi Z, Jiang L. 3.18-Acetic and Propionic Acids. In: Moo-Young M, editor. Comprehensive Biotechnology (Second Edition). Burlington: Academic Press; 2011. p. 189-199.

87. Lu PD, Yuan MC, Quan XP, et al. Preclinical studies of licorice in ulcerative colitis: A systematic review with meta-analysis and network pharmacology. J Ethnopharmacol. 2022 Oct 5; 296:115444.

88. Exploring the Significance of Microglial Phenotypes and Morphological Diversity in Neuroinflammation and Neurodegenerative Diseases: From Mechanisms to Potential Therapeutic Targets. Mai M. Anwar. 2024/06/05

What is claimed is:

1. A composition for self-nanoemulsifying drug delivery, comprising:

(a) an oil comprising Caraway oil;

(b) a surfactant comprising Tween 20;

(c) one or more active bioactive compounds comprising licorice extract;

(d) a co-emulsifier or solubilizer comprising propylene glycol; and (e) lyophilized milk kefir grains as a solid carrier for the one or more bioactive compounds, wherein the composition forms a self-nanoemulsifying self-nanosuspension (SNESNS) that spontaneously forms an oil-in-water nanoemulsion upon dilution with water under gentle stirring, and wherein the lyophilized milk kefir grains are loaded with the SNESNS to form a dual nanosystem comprising both a nanoemulsion phase and a nanosuspension phase.

2. The composition of claim 1, wherein the oil-in-water nanoemulsion has a size of up to about 200 nm upon dilution with water under gentle stirring, and wherein the nanosuspension phase comprises particles ranging in size from about 230 nm to about 300 nm.

3. The composition of claim 1, wherein the composition comprises about 30% Caraway oil, about 60% Tween 20, and about 10% propylene glycol (w/w), and wherein the licorice extract is present at a concentration of about 3 mg/mL.

4. A method for self-nanoemulsifying lyophilized milk kefir, comprising:

(a) obtaining milk kefir grain starters;

(b) adding the milk kefir grain starters to fully pasteurized milk'

(c) fermenting the milk at about 25° C. for about 24 hours;

(d) filtering the milk through a sterile plastic sieve;

(e) optionally storing the starter of the processed milk kefir grains under vacuum conditions at about 1 Pa and at a temperature of about −39° C. until needed for further use;

(f) lyophilizing the milk kefir grain (L-MKG) using a freeze-dryer and optionally storing the lyophilized grains until needed for further use;

(g) utilizing a ternary phase diagram for optimizing a ratio of formulation ingredients used for preparing a self-nano emulsifying system (SNES);

(h) obtaining a self-nanoemulsifying formulation selected by utilizing the ternary phase diagram;

(i) mixing Caraway oil, Tween 20, and propylene glycol in a formulation selected utilizing the ternary phase diagram;

(j) adding licorice extract to obtain a final formulation;

(k) mixing with a homogenizer for about 5 min to obtain a licorice-self-nanoemulsifying self-nanosuspension (SNESNS);

(l) adding the licorice-SNESNS dropwise to the milk kefir grains (L-MKGs) to obtain a homogenous dispersion;

(m) lyophilizing the dispersion under reduced pressure to obtain lyophilized milk kefir as solid carriers loaded with self-nanoemulsifying self-nanosuspension (L-MKG/SNESNS) in powder form.

5. The method of claim 4, wherein the grains are thoroughly washed with pasteurized milk before each new inoculation.

6. The method of claim 4, wherein the formulation selected utilizing the ternary phase diagram is selected from the group consisting of about 30% Caraway oil, about 60% Tween 20, and about 10% propylene glycole (w/w).

7. The method of claim 6, wherein licorice extract is added to the formulation to obtain the final formulation having a concentration of about 3 mg/mL.

8. The method of claim 6, wherein the final Tween 20 concentration is greater or equal to about 40%.

9. The method of claim 4, wherein a symbiotic mixture of microorganisms in kefir comprises bacterial strains *E. coli*, *Streptococcus mitis*, *Lactobacillus casei*, *Bacteroides fragilis*, or mixtures thereof.

10. A method for delivering one or more bioactive compounds to selectively target highly inflamed intestinal mucosa of a subject in need thereof, the method comprising administering the composition of claim 1 to the subject in need thereof.

11. The method of claim 10, wherein the oil-in-water nanoemulsion has a size of up to about 200 nm upon dilution with water under gentle stirring, and wherein the nanosuspension phase comprises particles ranging in size from about 230 nm to about 300 nm.

12. The method of claim 11, wherein the composition comprises about 30% Caraway oil, about 60% Tween 20, and about 10% propylene glycol (w/w), and wherein the licorice extract is present at a concentration of about 3 mg/mL.

13. The method of claim 12, wherein delivering the one or more bioactive compounds restores neurotransmitter levels and/or alleviates inflammatory processes in the subject in need thereof.

14. The method of claim 13, wherein delivering the one or more bioactive compounds improves the symptoms of chronic inflammatory bowel diseases (IBD) and/or manages IBD-related cognitive decline.

* * * * *